(12) United States Patent
Kim et al.

US011091515B2

(10) Patent No.: US 11,091,515 B2
(45) Date of Patent: Aug. 17, 2021

(54) POLYPEPTIDE DERIVED FROM CAP1 AND PHARMACEUTICAL COMPOSITION COMPRISING SAME AS EFFECTIVE INGREDIENT

(71) Applicant: Seoul National University Hospital, Seoul (KR)

(72) Inventors: Hyo Soo Kim, Seoul (KR); Hyun Duk Jang, Seoul (KR); Sang Eun Lee, Seoul (KR)

(73) Assignee: SEOUL NATIONAL UNIVERSITY HOSPITAL, Seoul (KR)

( * ) Notice: Subject to any disclaimer, the term of this patent is extended or adjusted under 35 U.S.C. 154(b) by 0 days.

(21) Appl. No.: 16/482,333

(22) PCT Filed: Jan. 31, 2018

(86) PCT No.: PCT/KR2018/001332
§ 371 (c)(1),
(2) Date: Jul. 31, 2019

(87) PCT Pub. No.: WO2018/143666
PCT Pub. Date: Aug. 9, 2018

(65) Prior Publication Data
US 2020/0157147 A1 May 21, 2020

(30) Foreign Application Priority Data
Jan. 31, 2017 (KR) .................. 10-2017-0014128

(51) Int. Cl.
| C07K 7/06 | (2006.01) |
| C07K 7/08 | (2006.01) |
| A61K 38/00 | (2006.01) |
| A61P 3/10 | (2006.01) |
| A61P 35/04 | (2006.01) |

(52) U.S. Cl.
CPC ........ *C07K 7/06* (2013.01); *A61P 3/10* (2018.01); *A61P 35/04* (2018.01); *C07K 7/08* (2013.01); *A61K 38/00* (2013.01)

(58) Field of Classification Search
None
See application file for complete search history.

(56) References Cited

U.S. PATENT DOCUMENTS

| 2011/0177029 A1* | 7/2011 | DeFrees ............. C07K 14/56 424/85.7 |
| 2012/0014973 A1 | 1/2012 | Naparstek et al. |
| 2014/0171489 A1* | 6/2014 | Park ................. G01N 33/6863 514/44 A |

FOREIGN PATENT DOCUMENTS

WO 2004034062 A2 4/2004

OTHER PUBLICATIONS

GenBank CAG33690.1 (Year: 2008).*
Lee et al. (Cell Metab. Mar. 4, 2014;19(3):484-97) (Year: 2014).*
Jamalludin et al. (Br J Pharmacol. Feb. 2012; 165(3): 622-632) (Year: 2012).*
Banerjee et al. (Science, Feb. 2, 20040;303(5661): 1195-8) (Year: 2004).*
International Search Report issued by the Korean Intellectual Property Office acting as International Searching Authority for International Application No. PCT/KR2018/001332 dated Jul. 24, 2018
Lee et al., "Adenylyl Cyclase-associated Protein 1 is a Receptor for Human Resistin and Mediates Inflammatory Actions of Human Monocytes", Cell Metabolism, vol. 19, pp. 484-497 (2014).
Freeman et al., "A Conserved Proline-Rich Region of the *Saccharomyces cerevisiae* Cyclase-Associated Protein Binds SH3 Domains and Modulates Cytoskeletal Localization", Molecular and Cellular Biology, vol. 16, No. 2, pp. 548-556 (1996).
NCBI, Genbank accession No. CAG33690.1 (Oct. 16, 2008).

* cited by examiner

*Primary Examiner* — Sergio Coffa
(74) *Attorney, Agent, or Firm* — Carter, DeLuca & Farrell LLP; George Likourezos; Carmella Stephens

(57) ABSTRACT

The present invention relates to a polypeptide derived from CAP1 and a pharmaceutical composition comprising the same as an effective ingredient and, more particularly, to a peptide including the amino acid sequence of SEQ ID NO: 1, any 0 to 20 amino acid residues added to the N terminus thereof, and any 0 to 75 amino acid residues added to the C terminus thereof, and a pharmaceutical composition comprising the peptide as an effective ingredient for the prevention and alleviation of inflammatory diseases, the inhibition of cancer and cancer metastasis, the prevention and alleviation of diabetes, the prevention and alleviation of arteriosclerosis or cardiovascular diseases, and the prevention and alleviation of heart failure. Exhibiting the effect of suppressing the binding of resistin to CAP1 and inhibiting NF-κB activity, the method of the present invention can be useful for treating inflammatory diseases, cancer, diabetes, arteriosclerosis, cardiovascular diseases, and heart failure which are caused by the activation of resistin and NF-κB.

7 Claims, 10 Drawing Sheets
(5 of 10 Drawing Sheet(s) Filed in Color)
Specification includes a Sequence Listing.

SEQUENCE LISTING

<160> NUMBER OF SEQ ID NOS: 31

<210> SEQ ID NO 1
<211> LENGTH: 10
<212> TYPE: PRT
<213> ORGANISM: Artificial Sequence
<220> FEATURE:
<223> OTHER INFORMATION: Synthetic: pep10 peptide

```
<400> SEQUENCE: 1

Gly Pro Pro Pro Pro Val Ser Thr Ser
1               5                   10

<210> SEQ ID NO 2
<211> LENGTH: 20
<212> TYPE: PRT
<213> ORGANISM: Artificial Sequence
<220> FEATURE:
<223> OTHER INFORMATION: Synthetic: VS peptide

<400> SEQUENCE: 2

Pro Pro Pro Pro Gly Pro Pro Pro Pro Val Ser Thr Ser Ser Gly
1               5                   10                  15

Ser Asp Glu Ser
            20

<210> SEQ ID NO 3
<211> LENGTH: 20
<212> TYPE: PRT
<213> ORGANISM: Artificial Sequence
<220> FEATURE:
<223> OTHER INFORMATION: Synthetic: AA peptide

<400> SEQUENCE: 3

Pro Pro Pro Pro Gly Pro Pro Pro Pro Ala Ala Thr Ser Ser Gly
1               5                   10                  15

Ser Asp Glu Ser
            20

<210> SEQ ID NO 4
<211> LENGTH: 20
<212> TYPE: PRT
<213> ORGANISM: Artificial Sequence
<220> FEATURE:
<223> OTHER INFORMATION: Synthetic: pro1A peptide

<400> SEQUENCE: 4

Ala Ala Ala Ala Gly Pro Pro Pro Pro Val Ser Thr Ser Ser Gly
1               5                   10                  15

Ser Asp Glu Ser
            20

<210> SEQ ID NO 5
<211> LENGTH: 20
<212> TYPE: PRT
<213> ORGANISM: Artificial Sequence
<220> FEATURE:
<223> OTHER INFORMATION: Synthetic: pro2A peptide

<400> SEQUENCE: 5

Pro Pro Pro Pro Gly Ala Ala Ala Ala Val Ser Thr Ser Ser Gly
1               5                   10                  15

Ser Asp Glu Ser
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic: AAA peptide

<400> SEQUENCE: 6
```

```
Ala Ala Ala Ala Gly Ala Ala Ala Ala Ala Thr Ser Ser Gly
1               5                   10                  15

Ser Asp Glu Ser
            20

<210> SEQ ID NO 7
<211> LENGTH: 3
<212> TYPE: PRT
<213> ORGANISM: Artificial Sequence
<220> FEATURE:
<223> OTHER INFORMATION: Synthetic: PVS peptide

<400> SEQUENCE: 7

Pro Val Ser
1

<210> SEQ ID NO 8
<211> LENGTH: 126
<212> TYPE: PRT
<213> ORGANISM: Artificial Sequence
<220> FEATURE:
<223> OTHER INFORMATION: Synthetic: SH3 Binding Amino Acid

<400> SEQUENCE: 8

Leu Ala Trp Ser Lys Thr Gly Pro Val Ala Lys Glu Leu Ser Gly Leu
1               5                   10                  15

Pro Ser Gly Pro Ser Ala Gly Ser Gly Pro Pro Pro Pro Pro Gly
            20                  25                  30

Pro Pro Pro Pro Pro Val Ser Thr Ser Ser Gly Ser Asp Glu Ser Ala
            35                  40                  45

Ser Arg Ser Ala Leu Phe Ala Gln Ile Asn Gln Gly Glu Ser Ile Thr
        50                  55                  60

His Ala Leu Lys His Val Ser Asp Asp Met Lys Thr His Lys Asn Pro
65                  70                  75                  80

Ala Leu Lys Ala Gln Ser Gly Pro Val Arg Ser Gly Pro Lys Pro Phe
                85                  90                  95

Ser Ala Pro Lys Pro Gln Thr Ser Pro Ser Pro Lys Arg Ala Thr Lys
            100                 105                 110

Lys Glu Pro Ala Val Leu Glu Leu Glu Gly Lys Lys Trp Arg
            115                 120                 125

<210> SEQ ID NO 9
<211> LENGTH: 378
<212> TYPE: DNA
<213> ORGANISM: Artificial Sequence
<220> FEATURE:
<223> OTHER INFORMATION: Synthetic: SH3 Binding Domain

<400> SEQUENCE: 9
ctggcctgga gcaaaacggg gcctgtggca aagaactga gcggactgcc atctggaccc      60
tctgccggat caggtcctcc tccccctcca ccaggccccc ctcctccccc agtctctacc    120
agttcaggct cagatgagtc tgcttcccgc tcagcactgt tcgcgcagat taatcagggg    180
gagagcatta cacatgccct gaaacatgta tctgatgaca tgaagactca caagaaccct    240
gccctgaagg ctcagagtgg tccagtacgc agtggcccca aaccattctc tgcacctaaa    300
ccccaaacca gcccatcccc caaacgagcc acaaagaagg agccagctgt acttgaactg    360
gagggcaaga agtggaga                                                  378

<210> SEQ ID NO 10
```

```
<211> LENGTH: 21
<212> TYPE: DNA
<213> ORGANISM: Artificial Sequence
<220> FEATURE:
<223> OTHER INFORMATION: Synthetic: mPEPCK forward

<400> SEQUENCE: 10
ggtatccgga ccacttcttg g                                             21

<210> SEQ ID NO 11
<211> LENGTH: 20
<212> TYPE: DNA
<213> ORGANISM: Artificial Sequence
<220> FEATURE:
<223> OTHER INFORMATION: Synthetic: mPEPCK reverse

<400> SEQUENCE: 11
ggggagcaag attagagccc                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic: mG6Pase forward

<400> SEQUENCE: 12
aagagcgcaa cagttccctt                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic: mG6Pase reverse

<400> SEQUENCE: 13
ctctggcctc acaatgggtt                                               20

<210> SEQ ID NO 14
<211> LENGTH: 21
<212> TYPE: DNA
<213> ORGANISM: Artificial Sequence
<220> FEATURE:
<223> OTHER INFORMATION: Synthetic: mPGC1a forward

<400> SEQUENCE: 14
gtgtgtgctg tgtgtcagag t                                             21

<210> SEQ ID NO 15
<211> LENGTH: 20
<212> TYPE: DNA
<213> ORGANISM: Artificial Sequence
<220> FEATURE:
<223> OTHER INFORMATION: Synthetic: mPGC1a reverse

<400> SEQUENCE: 15
accacttcaa tccacccaga                                               20

<210> SEQ ID NO 16
<211> LENGTH: 21
<212> TYPE: DNA
<213> ORGANISM: Artificial Sequence
<220> FEATURE:
<223> OTHER INFORMATION: Synthetic: mACC forward

<400> SEQUENCE: 16
```
aaaatgaagg ggaacgactg c					21

<210> SEQ ID NO 17
<211> LENGTH: 20
<212> TYPE: DNA
<213> ORGANISM: Artificial Sequence
<220> FEATURE:
<223> OTHER INFORMATION: Synthetic: mACC reverse

<400> SEQUENCE: 17
cagttctgcc tggaggaccc					20

<210> SEQ ID NO 18
<211> LENGTH: 20
<212> TYPE: DNA
<213> ORGANISM: Artificial Sequence
<220> FEATURE:
<223> OTHER INFORMATION: Synthetic: mFASN forward

<400> SEQUENCE: 18
aggtggcaga ggtgctggct					20

<210> SEQ ID NO 19
<211> LENGTH: 20
<212> TYPE: DNA
<213> ORGANISM: Artificial Sequence
<220> FEATURE:
<223> OTHER INFORMATION: Synthetic: mFASN reverse

<400> SEQUENCE: 19
gcgcagggtc ggaagggttc					20

<210> SEQ ID NO 20
<211> LENGTH: 20
<212> TYPE: DNA
<213> ORGANISM: Artificial Sequence
<220> FEATURE:
<223> OTHER INFORMATION: Synthetic: mSREBP1 forward

<400> SEQUENCE: 20
cccaagactg cacaatgctg					20

<210> SEQ ID NO 21
<211> LENGTH: 20
<212> TYPE: DNA
<213> ORGANISM: Artificial Sequence
<220> FEATURE:
<223> OTHER INFORMATION: Synthetic: mSREBP1 reverse

<400> SEQUENCE: 21
ctctcaggag agttggcacc					20

<210> SEQ ID NO 22
<211> LENGTH: 20
<212> TYPE: DNA
<213> ORGANISM: Artificial Sequence
<220> FEATURE:
<223> OTHER INFORMATION: Synthetic: mTNF-alpha forward

<400> SEQUENCE: 22
gtgacaagcc tgtagcccac					20

<210> SEQ ID NO 23
<211> LENGTH: 20
<212> TYPE: DNA

```
<213> ORGANISM: Artificial Sequence
<220> FEATURE:
<223> OTHER INFORMATION: Synthetic: mTNF-alpha reverse

<400> SEQUENCE: 23
gcagccttgt cccttgaaga                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic: mIL-6 forward

<400> SEQUENCE: 24
cggccttccc tacttcacaa                                              20

<210> SEQ ID NO 25
<211> LENGTH: 20
<212> TYPE: DNA
<213> ORGANISM: Artificial Sequence
<220> FEATURE:
<223> OTHER INFORMATION: Synthetic: mIL-6 reverse

<400> SEQUENCE: 25
tctgcaagtg catcatcgtt                                              20

<210> SEQ ID NO 26
<211> LENGTH: 20
<212> TYPE: DNA
<213> ORGANISM: Artificial Sequence
<220> FEATURE:
<223> OTHER INFORMATION: Synthetic: mIL-beta forward

<400> SEQUENCE: 26
caggcttgtg ctctgcttgt                                              20

<210> SEQ ID NO 27
<211> LENGTH: 20
<212> TYPE: DNA
<213> ORGANISM: Artificial Sequence
<220> FEATURE:
<223> OTHER INFORMATION: Synthetic: mIL-beta reverse

<400> SEQUENCE: 27
tgggcctcaa aggaaagaat                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic: MCP-1 forward

<400> SEQUENCE: 28
caggtccctg tcatgcttct                                              20

<210> SEQ ID NO 29
<211> LENGTH: 20
<212> TYPE: DNA
<213> ORGANISM: Artificial Sequence
<220> FEATURE:
<223> OTHER INFORMATION: Synthetic: MCP-1 reverse

<400> SEQUENCE: 29
cccattcctt cttggggtca                                              20
```

```
<210> SEQ ID NO 30
<211> LENGTH: 20
<212> TYPE: DNA
<213> ORGANISM: Artificial Sequence
<220> FEATURE:
<223> OTHER INFORMATION: Synthetic: CXCL5 forward

<400> SEQUENCE: 30
ccccttcctc agtcatagcc                                               20

<210> SEQ ID NO 31
<211> LENGTH: 21
<212> TYPE: DNA
<213> ORGANISM: Artificial Sequence
<220> FEATURE:
<223> OTHER INFORMATION: Synthetic: CXCL5 reverse

<400> SEQUENCE: 31
tggatccaga cagacctcct t                                             21
```

POLYPEPTIDE DERIVED FROM CAP1 AND PHARMACEUTICAL COMPOSITION COMPRISING SAME AS EFFECTIVE INGREDIENT

REFERENCE TO SEQUENCE LISTING SUBMITTED VIA EFS-WEB

This application includes an electronically submitted sequence listing in .txt format. The .txt file contains a sequence listing entitled "2650-5 PCT US_ST25.txt" created on Dec. 31, 2019 and is 8,485 bytes in size. The sequence listing contained in this .txt file is part of the specification and is hereby incorporated by reference herein in its entirety.

TECHNICAL FIELD

The present application claims priority from and the benefit of Korean Patent Application No. 10-2017-0014128 filed on 31 Jan. 2017, the disclosure of which is hereby incorporated herein by reference in its entirety.

The present invention relates to a polypeptide derived from CAP1 and a pharmaceutical composition containing same as an active ingredient. More specifically, the present invention relates to a peptide consisting of an amino acid sequence comprising the amino acid sequence of SEQ ID NO: 1 (GPPPPPVSTS) with 0-20 amino acids added to the N-terminus thereof and 0-75 amino acids added to the C-terminus thereof, and to a pharmaceutical composition comprising the peptide as an active ingredient for preventing and alleviating an inflammatory disease, for anti-cancer and anti-metastasis, for preventing and alleviating diabetes, for preventing and alleviating atherosclerosis or a cardiovascular disease, or for preventing and alleviating a heart failure.

BACKGROUND ART

Resistin was first identified as a mediator that induces insulin tolerance and is expressed in mature adipocytes in obese mice. Resistin belongs to a family of cysteine-rich proteins, known also as a representative of resistin-like molecules (RELMs), and acts to induce inflammation. Murine resistin is known to be involved in the pathogenesis of obesity-mediated insulin tolerance and type 2 diabetes (Li et al., *Endocrine* 35, 243-251. 2009; Nakata et al., *Biochem. Biophys. Res. Commun.* 353, 1046-1051. 2007; Steppan et al., *Nature,* 409, 307-312. 2001).

The protein sequence of human resistin is only about 60% identical to that of mouse resistin. Mouse resistin is first expressed in and secreted from mainly mature adipocytes, while human resistin is mainly secreted from peripheral blood mononuclear cells (PBMCs), represented by leukocytes, and macrophages. Many studies have established that the roles of human resistin are different from those of mouse resistin.

Human resistin has been reported to encourage the recruitment of immune cells and induce the secretion of pro-inflammatory factors, and evidence are reported to induce inflammatory diseases and atherosclerosis separately from the aggravation of insulin tolerance (Bokarewa et al., *J. Immunol.* 174, 5789-5795. 2005; Silswal et al., *Biochem. Biophys. Res. Commun.* 334, 1092-1101. 2005; Burnett et al., *Atherosclerosis* 182, 241-248. 2005; Jung et al., *Cardiovasc. Res.* 69, 76-85. 2006; Reilly et al., *Circulation* 111, 932-939. 2005).

Resistin, which is present in both murine and human atherosclerosis lesions, is known to be as an inflammatory indicator of atherosclerosis in humans and is known to aggravate atherosclerosis by activating monocytes (Cho et al., *J. Am. Coll. Cardiol.* 57, 99-109. 2011). Therefore, human resistin is thought to be a core element to stimulate monocytes causing atherosclerosis.

The mechanism of inflammation induction by human resistin is the activation of nuclear factor kappa B (NF-κB) transcription factor.

The present inventors, after five years of research, first discovered adenylyl cyclase-associated protein 1 (CAP1), which is a receptor that interacts directly with human resistin (Lee S et at., *Cell Metabolism,* 19(3): 484-97, 2014).

Therefore, the use of CAP1, a receptor to mediate actions of human resistin, allows the development of medicines for diseases caused by resistin.

DETAILED DESCRIPTION OF THE INVENTION

Technical Problem

Therefore, to inhibit the binding of resistin and CAP1, the present inventors produced a peptide containing a proline-rich region, valine at position 27, and serine at position 28 in the SH3 domain of CAP1 to which resistin binds, and thus completed the present invention.

Accordingly, an aspect of the present invention is to provide a peptide consisting of an amino acid sequence which comprises the amino acid sequence of SEQ ID NO: 1 (GPPPPPVSTS) with 0-20 amino acids added to the N-terminus thereof and 0-75 amino acids added to the C-terminus thereof.

Another aspect of the present invention is to provide a composition for treating an inflammatory disease, the composition comprising the peptide as an active ingredient.

Another aspect of the present invention is to provide a composition for treating an inflammatory disease, the composition consisting of the peptide.

Another aspect of the present invention is to provide a composition for treatment of an inflammatory disease, the composition consisting essentially of the peptide.

Still another aspect of the present invention is to provide a composition for anti-cancer and anti-metastasis, the composition comprising the peptide as an active ingredient.

Still another aspect of the present invention is to provide a composition for anti-cancer and anti-metastasis, the composition consisting of the peptide.

Still another aspect of the present invention is to provide a composition for anti-cancer and anti-metastasis, the composition consisting essentially of the peptide.

Still another aspect of the present invention is to provide a composition for treating diabetes, the composition comprising the peptide as an active ingredient.

Still another aspect of the present invention is to provide a composition for treating diabetes, the composition consisting of the peptide.

Still another aspect of the present invention is to provide a composition for treating diabetes, the composition consisting essentially of the peptide.

Still another aspect of the present invention is to provide a composition for treating atherosclerosis or a cardiovascular disorder, the composition comprising the peptide as an active ingredient.

Still another aspect of the present invention is to provide a composition for treating atherosclerosis or a cardiovascular disorder, the composition consisting of the peptide.

Still another aspect of the present invention is to provide a composition for treating atherosclerosis or a cardiovascular disorder, the composition consisting essentially of the peptide.

Still another aspect of the present invention is to provide a composition for treating a heart failure, the composition comprising the peptide as an active ingredient.

Still another aspect of the present invention is to provide a composition for treating a heart failure, the composition consisting of the peptide.

Still another aspect of the present invention is to provide a composition for treating a heart failure, the composition consisting essentially of the peptide.

Still another aspect of the present invention is to provide use of the peptide for preparing an agent for treating an inflammatory disease.

Still another aspect of the present invention is to provide method for treating an inflammatory disease in a subject in need thereof, the method comprising administering the peptide to the subject in an amount effective for treating the inflammatory disease in the subject.

Still another aspect of the present invention is to provide use of the peptide for preparing an agent for anti-cancer and anti-metastasis.

Still another aspect of the present invention is to provide a method for anti-cancer and anti-metastasis in a subject in need thereof, the method comprising administering the peptide to the subject in an amount effective for anti-cancer and anti-metastasis in the subject.

Still another aspect of the present invention is to provide use of the peptide for preparing an agent for treating diabetes.

Still another aspect of the present invention is to provide a method for treating diabetes in a subject in need thereof, the method comprising administering the peptide to the subject in an amount effective for treating diabetes in the subject.

Still another aspect of the present invention is to provide use of the peptide for preparing an agent for treating atherosclerosis or a cardiovascular disorder.

Still another aspect of the present invention is to provide a method for treating atherosclerosis or a cardiovascular disorder in a subject in need thereof, the method comprising administering the peptide to the subject in an amount effective for treating atherosclerosis or a cardiovascular disorder in the subject.

Still another aspect of the present invention is to provide use of the peptide for preparing an agent for treating a heart failure.

Still another aspect of the present invention is to provide a method for treating a heart failure in a subject in need thereof, the method comprising administering the peptide to the subject in an amount effective for treating a heart failure in the subject.

Technical Solution

In accordance with an aspect of the present invention, there is provided a peptide consisting of an amino acid sequence which comprises the amino acid sequence of SEQ ID NO: 1 (GPPPPPVSTS) with 0-20 amino acids added to the N-terminus thereof and 0-75 amino acids added to the C-terminus thereof.

In accordance with another aspect of the present invention, there is provided a composition for treating an inflammatory disease, the composition comprising the peptide as an active ingredient.

In accordance with another aspect of the present invention, there is provided a composition for treating an inflammatory disease, the composition consisting of the peptide.

In accordance with another aspect of the present invention, there is provided a composition for treating an inflammatory disease, the composition consisting essentially of the peptide.

In accordance with still another aspect of the present invention, there is provided a composition for anti-cancer and anti-metastasis, the composition comprising the peptide as an active ingredient.

In accordance with still another aspect of the present invention, there is provided a composition for anti-cancer and anti-metastasis, the composition consisting of the peptide.

In accordance with still another aspect of the present invention, there is provided a composition for anti-cancer and anti-metastasis, the composition consisting essentially of the peptide.

In accordance with still another aspect of the present invention, there is provided a composition for treating diabetes, the composition comprising the peptide as an active ingredient.

In accordance with still another aspect of the present invention, there is provided a composition for treating diabetes, the composition consisting of the peptide.

In accordance with still another aspect of the present invention, there is provided a composition for treating diabetes, the composition consisting essentially of the peptide.

In accordance with still another aspect of the present invention, there is provided a composition for treating atherosclerosis or a cardiovascular disorder, the composition comprising the peptide as an active ingredient.

In accordance with still another aspect of the present invention, there is provided a composition for treating atherosclerosis or a cardiovascular disorder, the composition consisting of the peptide.

In accordance with still another aspect of the present invention, there is provided a composition for treating atherosclerosis or a cardiovascular disorder, the composition consisting essentially of the peptide.

In accordance with still another aspect of the present invention, there is provided a composition for treating a heart failure, the composition comprising the peptide as an active ingredient.

In accordance with still another aspect of the present invention, there is provided a composition for treating a heart failure, the composition consisting of the peptide.

In accordance with still another aspect of the present invention, there is provided a composition for treating a heart failure, the composition consisting essentially of the peptide.

In accordance with still another aspect of the present invention, there is provided use of the peptide for preparing an agent for treating an inflammatory disease.

In accordance with still another aspect of the present invention, there is provided a method for treating an inflammatory disease in a subject in need thereof, the method comprising administering the peptide to the subject in an amount effective for treating the inflammatory disease in the subject.

In accordance with still another aspect of the present invention, there is provided use of the peptide for preparing an agent for anti-cancer and anti-metastasis.

In accordance with still another aspect of the present invention, there is provided a method for anti-cancer and anti-metastasis in a subject in need thereof, the method comprising administering the peptide to the subject in an amount effective for anti-cancer and anti-metastasis in the subject.

In accordance with still another aspect of the present invention, there is provided use of the peptide for preparing an agent for treating diabetes.

In accordance with still another aspect of the present invention, there is provided a method for treating diabetes in a subject in need thereof, the method comprising administering the peptide to the subject in an amount effective for treating diabetes in the subject.

In accordance with still another aspect of the present invention, there is provided use of the peptide for preparing an agent for treating atherosclerosis or a cardiovascular disorder.

In accordance with still another aspect of the present invention, there is provided a method for treating atherosclerosis or a cardiovascular disorder in a subject in need thereof, the method comprising administering the peptide to the subject in an amount effective for treating atherosclerosis or a cardiovascular disorder in the subject.

In accordance with still another aspect of the present invention, there is provided use of the peptide for preparing an agent for treating a heart failure.

In accordance with still another aspect of the present invention, there is provided a method for treating a heart failure in a subject in need thereof, the method comprising administering the peptide to the subject in an amount effective for treating a heart failure in the subject.

Hereinafter, the present invention will be described in detail.

The present invention provides a peptide consisting of an amino acid sequence which comprises the amino acid sequence of SEQ ID NO: 1 (GPPPPPVSTS) with 0-20 amino acids added to the N-terminus thereof and 0-75 amino acids added to the C-terminus thereof.

In an example, a peptide comprising the amino acid sequence of SEQ ID NO: 1 (GPPPPPVSTS) was produced (see Table 1). THP-1 cell lysates were treated with mFC-resistin, treated with each of the peptides on Table 1, and subjected to pull down assay, and as a result, it could be confirmed that the treatment with the peptides of SEQ ID NOS: 1, 2, 4, and 5 inhibited the binding of resistin and CAP1 compared with control (see FIG. 6). Out of these, the peptide of SEQ ID NO: 2 was selected as a representative peptide.

In the present invention, the peptide inhibits the binding of adenylyl cyclase associated protein 1 (CAP1) and resistin. More preferably, the inhibition is a competitive inhibition.

As used herein, "adenylyl cyclase associated protein 1 (CAP1)" is a functional receptor of human resistin, and structurally and functionally divided into three domains. First, the highly conserved carboxyl-terminal domain binds with monomeric actin, and is essential in normal cellular morphology. Second, the amino-terminal domain of CAP1 interacts with adenylyl cyclase in yeast. Third, the centrally-located proline-rich domain interacts with Src homology 3 (SH3) domains of specific proteins (see FIG. 1).

As used herein, "resistin" is a cytokine defined as a mediator to induce insulin tolerance in obese mice, belongs to a family of cysteine-rich proteins, and is known as resistin-like molecules (RELMs). Murine resistin is involved in the pathogenesis of obesity-mediated insulin tolerance and type 2 diabetes and the regulation of inflammation. Human resistin is a hormone secreted from human monocytes, and causes chronic inflammation to act as a main causative substance of adult diseases, such as obesity, atherosclerosis, and diabetes.

In an example of the present invention, to investigate the binding inhibitory effect of the peptide in vitro, THP-1 cell lysates were mixed with mFC-hResistin and VS_peptide (SEQ ID NO: 2), and the resistin proteins were pulled down using Fc beads, and the binding of resistin and CAP1 was investigated by western blotting with an anti-CAP1 antibody. As a result, it could be confirmed that the binding of resistin and CAP1 was reduced by the treatment with VS_peptide (SEQ ID NO: 2) (see Example 1-2 and FIG. 3). To investigate binding inhibitory effect of the peptide in vivo, THP1 cells were treated with the peptide and immunoprecipitated with an CAP1 antibody. As a result, CAP1 effectively bound with resistin in cells, but when the cells were treated with VS_peptide (SEQ ID NO: 2), no bands were observed, indicating that the binding was inhibited (see Example 1-3 and FIG. 4). It was also confirmed through competitive ELISA that VS_peptide (SEQ ID NO: 2) effectively inhibited the binding of resistin and CAP1. It was investigated whether the binding of resistin and CAP1 was inhibited, by adding mFc-hResistin protein and various concentrations of VS_peptide (SEQ ID NO: 2) to a 96-well plate coated with the recombinant protein rhCAP1. The binding of mFc-Resistin and rhCAP1 was investigated by ELISA with the Fc-HRP secondary antibody. In cases where VS_peptide (SEQ ID NO: 2) was added, the more the peptide was added, the lower the OD value (see Example 1-4 and FIG. 5). It could be confirmed through these results that the VS_peptide (SEQ ID NO: 2) inhibited the binding of resistin and CAP1 in a dose-dependent manner.

In the present invention, the peptide is a peptide selected from the group consisting of a peptide of the amino acid sequence of SEQ ID NO: 1 (GPPPPPVSTS), a peptide of the amino acid sequence of SEQ ID NO: 2 (PPPPGPPPPPVST-SSGSDES), a peptide of the amino acid sequence of SEQ ID NO: 4 (AAAAGPPPPPVSTSSGSDES), a peptide of the amino acid sequence of SEQ ID NO: 5 (PPPP-GAAAAAVSTSSGSDES), a peptide of the amino acid sequence of SEQ ID NO: 6 (AAAAGAAAAAAATSSGS-DES), and a peptide consisting of 10-105 amino acids which comprises the $32^{nd}$ to $41^{st}$ amino acid residues in the $12^{th}$ to $116^{th}$ amino acid residues of SEQ ID NO: 8 (the SRC homology 3 domain (SH3 domain) of adenylyl cyclase associated protein 1 (CAP1)).

As used herein, "SH3 domains" are found in a plurality of different proteins involved in intracellular signaling and cytoskeletal organization (Cohen et al., *Cell* 80 (2): 237-48, 1995). Despite the diversity of the primary structure of the domain, this SH3 domain is common in the binding pattern to proteins having very similar overall structures and the minimal consensus sequence PxxP, a key determinant for native SH3 binding. One of the important functions of the SH3 domains is to participate in highly selective protein-protein interactions. The peptide of the present invention corresponds to the SH3 domain of CAP1 and is a resistin binding site of CAP1.

The present invention provides a peptide consisting of an amino acid sequence which comprises the amino acid sequence of SEQ ID NO: 1 (GPPPPPVSTS) with 0, 1, 2, 3, 4, 5, 6, 7, 8, 9, 10, 11, 12, 13, 14, 15, 16, 17, 18, 19, or 20 amino acids added to the N-terminus thereof and 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 amino acids added to the C-terminus thereof. The present invention provides, preferably, a peptide consisting of an amino acid sequence having 0 to 10 amino acids added to the N-terminus thereof and 0 to 20 amino acids added to the C-terminus thereof, and most preferably, a peptide consisting of an amino acid sequence having 4 amino acids added to the N-terminus thereof and 6 amino acids added to the C-terminus thereof.

The amino acid added to the N-terminus thereof may be proline or alanine, while the amino acid added to the C-terminus thereof may be serine, glycine, aspartate, or glutamate. More preferably, no amino acid may be added to the N-terminus thereof, or the amino acid(s) at position(s) 12-31, 13-31, 14-31, 15-31, 16-31, 17-31, 18-31, 19-31, 20-31, 21-31, 22-31, 23-31, 24-31, 25-31, 26-31, 27-31, 28-31, 29-31, 30-31, or 31 in SEQ ID NO: 8 may be added to the N-terminus thereof. No amino acid may be added to the C-terminus thereof, or the amino acid(s) at position(s) 42, 42-43, 42-44, 42-45, 42-46, 42-47, 42-48, 42-49, 42-50, 42-51, 42-52, 42-53, 42-54, 42-55, 42-56, 42-57, 42-58, 42-59, 42-60, 42-61, 42-62, 42-63, 42-64, 42-65, 42-66, 42-67, 42-68, 42-69, 42-70, 42-71, 42-72, 42-73, 42-74, 42-75, 42-76, 42-77, 42-78, 42-79, 42-80, 42-81, 42-82, 42-83, 42-84, 42-85, 42-86, 42-87, 42-88, 42-89, 42-90, 42-91, 42-92, 42-93, 42-94, 42-95, 42-96, 42-97, 42-98, 42-99, 42-100, 42-101, 42-102, 42-103, 42-104, 42-105, 42-106, 42-107, 42-108, 42-109, 42-110, 42-111, 42-112, 42-113, 42-114, 42-115, or 42-116 in SEQ ID NO: 8 may be added to the C-terminus thereof.

The peptide comprising the amino acid sequence of SEQ ID NO: 1 according to the present invention is characterized by containing proline, valine at position 27, and serine at position 28 in the SH3 domain of adenylyl cyclase associated protein 1 (CAP1).

In another example of the present invention, to investigate a core site of the VS_peptide (SEQ ID NO: 2), which inhibits the binding of resistin and CAP1, six types of peptides were further synthesized by substituting the proline-rich region, valine at position 27 (Val 27), and serine at position 28 (Ser 28) with alanine (A) (see Table 1). To investigate the ability of each of the peptides to inhibit the binding of resistin and CAP1, THP-1 cell lysates were treated with each peptide and subjected to pull down assay, and as a result, the treatment with the peptides of SEQ ID NOS: 1, 2, 4, and 5 effectively inhibited the binding of resistin and CAP1. It could be confirmed through these results that the core site of the VS_peptide (SEQ ID NO: 2), which inhibits the binding of resistin and CAP1, are Val 27 and Ser 28 (see Example 2 and FIG. 6).

The peptide of the present invention is characterized by inhibiting the activity of nuclear factor kappa B (NF-κB).

As used herein, "nuclear factor kappa B (NF-κB)" is a protein complex involved in inflammation regulation, immune modulation, apoptosis, cell proliferation, epithelial differentiation, and the like. NF-κB controls the expression of various genes and forms the central axis of intracellular signaling systems. In addition, NF-κB is classified into five types of subgroups, p50/p105(NF-κB1), p52/p100(NF-κB2), c-Rel, RelB, and p65 (RelA) This NF-κB types form several forms of homo-dimers or hetero-dimers in cells. Such dimers migrate into nuclei to stimulate the expression of the proteins, and the dimers are inactivated by binding with inhibitor kB (IκB) proteins in cytoplasm in the absence of external stimuli.

In still another example of the present invention, THP-1 cells were treated with resistin to activate NF-κB and treated with VS_peptide (SEQ ID NO: 2) and AA_peptide (SEQ ID NO: 3)] in which Val 27 and Ser 28, core sites for binding, were substituted with alanine, and then western blotting was conducted to investigate NF-κB activity through p65. The treatment with resistin effectively phosphorylated p65, while p65 was not phosphorylated by the addition of VS_peptide (SEQ ID NO: 2). The treatment with AA_peptide (SEQ ID NO: 3) with substitution of AA did not inhibit p65 phosphorylation activated by resistin. It can be seen through these results that VS_peptide (SEQ ID NO: 2) effectively inhibited NF-κB activity through Val 27 and Ser 28 (see Example 3 and FIG. 7).

The peptide of the present invention is characterized by inducing the activity of AMP activated protein kinase (AMPK).

As used herein, "AMPK" is an enzyme that plays a sensor role in intracellular energy homeostasis. When intracellular energy is reduced by metabolic stress or exercise, AMPK is activated to inhibit fatty acid synthesis and cholesterol synthesis, which are ATP-consuming processes, and promote ATP production. The activation of AMPK accelerates fatty acid oxidation in the liver, promotes fatty acid oxidation and glucose uptake in skeletal muscles, and is closely associated with adipogenesis inhibition and adipolysis in adipocytes and energy metabolism regulation promoting insulin secretion in pancreatic beta cells.

Resistin, as used herein, reduces the activation of AMPK (Banerjee RR et al., *Science*. 2004 Feb. 20; 303(5661); 1195-8). In an example of the present invention, the phosphorylation of AMPK induced by AICAR in HepG2 cells was reduced by resistin treatment, and the phosphorylation was effectively recovered by VS_peptide (SEQ ID NO: 2), while the phosphorylation was not accomplished by AA_peptide (SEQ ID NO: 3). As a result of confirming the phosphorylation of ACC known as an AMPK substrate, the phosphorylation was effectively increased by VS_peptide (SEQ ID NO: 2). The amount of LDL-cholesterol receptors was reduced by resistin treatment and again increased by VS_peptide (SEQ ID NO: 2) treatment, suggesting the reduction of LDL-cholesterol in blood (see Example 4 and FIG. 8).

The peptide of the present invention is characterized by inhibiting the activity of protein kinase A (PKA).

As used herein, "protein kinase A (PKA)" is cAMP-dependent protein kinase, and is one of the important enzymes for posttranscriptional modifications. PKA is present mainly in an inactivation state in the absence of cAMP, and activated by an increased intracellular cAMP to perform various phosphorylation reactions. In addition, PKA is used as a prototype of another protein kinase and plays important roles in various biological procedures, such as cell proliferation, metabolism, gene induction, angiogenesis, ion channel regulation, and apoptosis.

In the present invention, resistin acts to activate PKA. In an example of the present invention, VS_peptide (SEQ ID NO: 2) inhibits the activity of resistin by inhibiting the binding of resistin and CAP1 (see Example 1). Therefore, the peptide of the present invention inhibits PKA activity.

The present invention provides a composition for treating an inflammatory disease, the composition containing the peptide comprising SEQ ID NO: 1 as an active ingredient.

Further, the present invention provides a composition for treating an inflammatory disease, the composition consisting of the peptide containing SEQ ID NO: 1.

Furthermore, the present invention provides a composition for treating an inflammatory disease, the composition consisting essentially of the peptide containing SEQ ID NO: 1.

As used herein, the "inflammatory disease" includes, atopic dermatitis, psoriasis, sinusitis, rhinitis, conjunctivitis, asthma, dermatitis, inflammatory collagen vascular disease, glomerulonephritis, encephalitis, inflammatory bowel disease, chronic obstructive pulmonary disease, sepsis, septic shock, pulmonary fibrosis, undifferentiated spondylarthrosis, undifferentiated arthropathy, arthritis, inflammatory osteolysis, chronic inflammatory diseases caused by viral or bacterial infection, colitis, ulcerative colitis, inflammatory bowel disease, type 1 diabetes, type 2 diabetes, arthritis, rheumatoid arthritis, reactive arthritis, osteoarthritis, psoriasis, scleroderma, osteoporosis, atherosclerosis, myocarditis, endocarditis, pericarditis, cystic fibrosis, Hashimoto thyroiditis, Graves' disease, leprosy, syphilis, Lyme disease, borreliosis, neurogenic borreliosis, tuberculosis, sarcoidosis, lupus, discoid lupus, chilblain lupus, lupus nephritis, systemic lupus erythematosus, macular degeneration, uveitis, irritable bowel syndrome, Crohn's disease, Sjogren's syndrome, fibromyalgia, chronic fatigue syndrome, chronic fatigue and immune dysfunction syndrome, myalgic encephalomyelitis, amyotrophic lateral sclerosis, Parkinson's disease, and multiple sclerosis, but is not limited thereto.

In an example of the present invention, it was confirmed that VS_peptide (SEQ ID NO: 2) effectively inhibited the phosphorylation of p65 by resistin (see Example 3 and FIG. 7). These results showed that VS_peptide (SEQ ID NO: 2) is effective for an inflammatory disease by inhibiting NF-κB that regulates inflammation.

The present invention provides a composition for anti-cancer and anti-metastasis, the composition comprising the peptide containing SEQ ID NO: 1 as an active ingredient.

Furthermore, the present invention provides a composition for anti-cancer and anti-metastasis, the composition consisting of the peptide containing SEQ ID NO: 1.

Furthermore, the present invention provides a composition for anti-cancer and anti-metastasis, the composition consisting essentially of the peptide containing SEQ ID NO: 1.

As used herein, the "cancer" may be selected from the group consisting of breast cancer, colorectal cancer, lung cancer, small cell lung cancer, gastric cancer, liver cancer, blood cancer, bone cancer, pancreatic cancer, skin cancer, head or neck cancer, cutaneous or intraocular melanoma, eye tumor, peritoneal cancer, uterine cancer, ovarian cancer, rectal cancer, anal cancer, colon cancer, fallopian tube carcinoma, endometrial carcinoma, cervical cancer, vaginal cancer, vulvar carcinoma, Hodgkin's disease, esophageal cancer, small intestine cancer, endocrine cancer, thyroid cancer, parathyroid carcinoma, adrenal cancer, soft tissue sarcoma, urethral cancer, penis cancer, prostate cancer, testicular cancer, oral cancer, gallbladder cancer, cholangiocarcinoma, chronic or acute leukemia, lymphocyte lymphoma, bladder cancer, kidney cancer, ureteral cancer, renal cell carcinoma, renal pelvic carcinoma, CNS tumor, primary CNS lymphoma, spinal cord tumor, brain stem glioma, and pituitary adenoma, but is not limited thereto.

In still another example of the present invention, breast cancer cells were placed in a 24-well plate, resistin was added, VS_peptide (SEQ ID NO: 2) and AA_peptide (SEQ ID NO: 3) were added at 30 μM and 50 μM, respectively, followed by incubation, and then microscopic observation was performed. As a result, the extent of cell migration was less in the treatment with VS_peptide (SEQ ID NO: 2) compared to the treatment with AA_peptide (SEQ ID NO: 3], confirming that VS_peptide (SEQ ID NO: 2) inhibits the migration of cancer cells (see Example 4 and FIG. 9).

In still another example of the present invention, mice were administered with a peptide medicine in which albumin is conjugated to VS_peptide (SEQ ID NO: 2), and then the concentration of the medicine in the mouse body was investigated. As a result, the medicine was removed in the body within 4 hours when VS_peptide (SEQ ID NO: 2) was administered, while the medicine was left in the body even after 24 hours when albumin-conjugated VS_peptide (SEQ ID NO: 2) was administered (see Example 5 and FIG. 10).

The present invention provides a composition for treating diabetes, the composition comprising the peptide containing SEQ ID NO: 1 as an active ingredient.

Furthermore, the present invention provides a composition for treating diabetes, the composition consisting of the peptide containing SEQ ID NO: 1.

Furthermore, the present invention provides a composition for treating diabetes, the composition consisting essentially of the peptide containing SEQ ID NO: 1.

As used herein, "diabetes" is a metabolic disease in which high blood glucose levels last for a long period of time, and classified into type 1 diabetes and type 2 diabetes. Type 1 diabetes is characterized by insulin deficiency, and caused by insulin loss due to autoimmune disease or by nature. Type 2 diabetes shows insulin tolerance, and is caused by lifestyle, such as obesity, lack of exercise, or stress, or by heredity.

As described herein, resistin acts as a major causative substance of diabetes. An example of the present invention showed that VS_peptide (SEQ ID NO: 2) inhibits resistin activity by inhibiting the binding of resistin, secreted from mast cells, and CAP1 (see Example 1), and thus is effective in the prevention and treatment of diabetes.

In still another example of the present invention, mouse models fed with a high fat diet were intravenously administered with VS_peptide (SEQ ID NO: 2) and AA_peptide (SEQ ID NO: 3, Control), and then subjected to blood collection at 0, 15, 30, 60, and 120 minutes to measure blood glucose level changes. As a result, in the group administered with VS_peptide (SEQ ID NO: 2), the fasting blood glucose itself was low, and the blood glucose was effectively dropped 15 minutes after insulin injection, which indicates that the VS_peptide (SEQ ID NO: 2) has effects of lowering the blood glucose itself in blood and promptly controlling blood glucose by insulin (see Examples 6-3 and FIG. 14).

The present invention provides a composition for treating atherosclerosis or a cardiovascular disorder, the composition comprising the peptide containing SEQ ID NO: 1 as an active ingredient.

Furthermore, the present invention provides a composition for treating atherosclerosis or a cardiovascular disorder, the composition consisting of the peptide containing SEQ ID NO: 1.

Furthermore, the present invention provides a composition for treating atherosclerosis or a cardiovascular disorder, the composition consisting essentially of the peptide containing SEQ ID NO: 1.

As used herein, "atherosclerosis" is a disease in which arteries are narrowed for several reasons, such as decreased arterial elasticity or blood clots generated in the arteries. Atherosclerosis causes stroke, myocardial infarction, angina pectoris, and peripheral vascular diseases. Atherosclerosis is caused by hypertension, smoking, diabetes, obesity, or the like. According to the present invention, VS_peptide (SEQ ID NO: 2) suppresses the occurrence of atherosclerosis by inhibiting the binding of resistin and CAP1.

As used herein, "cardiovascular disease" is a disease that occurs in the heart and main arteries, and includes hypertension, ischemic heart disease, coronary artery disease, angina pectoris, myocardial infarction, stroke, arrhythmia, and the like. Cardiovascular disease is caused by age, diabetes, obesity, smoking, or the like. As described herein, while the cardiovascular disease may be caused by the activity of resistin secreted from mast cells, VS_peptide (SEQ ID NO: 2) inhibits the binding of resistin and CAP1 to inhibit resistin activity, and thus can be effective for treating cardiovascular disease.

The present invention provides a composition for treating a heart failure, the composition comprising the peptide containing SEQ ID NO: 1 as an active ingredient.

Furthermore, the present invention provides a composition for treating a heart failure, the composition consisting of the peptide containing SEQ ID NO: 1.

Furthermore, the present invention provides a composition for treating a heart failure, the composition consisting essentially of the peptide containing SEQ ID NO: 1.

As used herein, "heart failure" is a disease that is caused by the insufficient supply of blood necessary for body tissues, resulting from the reduction in filling function (diastolic function) of the heart to receive blood or pumping function (systolic function) of the heart to press blood due to heart structural or functional abnormality. Heart failure is caused by a cardiovascular disease, a heart muscle disease, hypertension, a valvular disease, tachycardia, stress, or the like. In the present invention, VS_peptide (SEQ ID NO: 2) inhibits resistin activity by inhibiting the binding of resistin and CAP1, and thus is effective for treating heart failure.

As described above, it is known as described above that resistin is a main cause of atherosclerosis or a cardiovascular disease and activates monocytes to aggravate atherosclerosis. An example of the present invention showed that VS_peptide (SEQ ID NO: 2) inhibits resistin activity by inhibiting the binding of resistin secreted from mast cells and CAP1 (see Example 1), and thus is effective in the prevention and treatment of atherosclerosis or a cardiovascular disease.

In a still another example of the present invention, mouse models fed with a high fat diet were intravenously administered with VS_peptide (SEQ ID NO: 2) and AA_peptide (SEQ ID NO: 3, Control) and sacrificed on Week 20, and then the liver and adipose tissues were harvested therefrom. The liver tissues were subjected to H&E staining (see Example 6-1), and the adipose tissues were subjected to immunohistochemistry staining with CD11b, which is a marker of macrophages (see Example 6-2).

The term "pharmaceutically acceptable" composition refers to a non-toxic composition that is physiologically acceptable, does not inhibit an action of an active ingredient when administered to a human being, and does not usually cause an allergic response or similar responses, such as gastroenteric troubles and dizziness. The pharmaceutical composition of the present invention may be variously formulated, together with a pharmaceutically acceptable carrier, to exhibit synergistic effect of immunomodulation or immunosuppression of combined administration of mTOR inhibitor and metformin, depending on the route of administration, by a method known in the art. The carrier includes all kinds of solvents, dispersion media, oil-in-water or water-in-oil emulsions, aqueous compositions, liposomes, microbeads, and microsomes.

The route of administration may be an oral or parenteral route. The parental administration may be, but is not limited to, intravenous, intramuscular, intra-arterial, intramedullary, intradural, intracardiac, transdermal, subcutaneous, intraperitoneal, intranasal, intestinal, topical, sublingual, or rectal administration.

The pharmaceutical composition of the present invention, when orally administered, may be formulated, together with a suitable carrier for oral administration, in the form of a powder, granules, a tablet, a pill, a sugar coated tablet, a capsule, a liquid, a gel, a syrup, a suspension, a wafer, or the like by a method known in the art. Examples of the suitable carrier may include: saccharides including lactose, dextrose, sucrose, sorbitol, mannitol, xylitol, erythritol, and maltitol; starches including corn starch, wheat starch, rice starch, and potato starch; celluloses including cellulose, methyl cellulose, sodium carboxy methyl cellulose, and hydroxypropyl methyl cellulose; and fillers, such as gelatin and polyvinyl pyrrolidone. In some cases, cross-linked polyvinyl pyrrolidone, agar, alginic acid, sodium alginate, or the like may be added as a disintegrant. Furthermore, the pharmaceutical composition may further contain an anti-coagulant, a lubricant, a wetting agent, an aroma, an emulsifier, a preservative, and the like.

As for the parenteral administration, the pharmaceutical composition of the present invention may be formulated in a dosage form of an injection, a transdermal administration preparation, and a nasal inhalant, together with a suitable parenteral carrier, by a method known in the art. The injection needs to be essentially sterilized, and needs to be protected from the contamination of microorganisms, such as bacteria and fungus. Examples of the suitable carrier for the injection may be a solvent or a dispersion medium, including water, ethanol, a polyol (e.g., glycerol, propylene glycol, liquid polyethylene glycol, etc.), a mixture thereof, and/or vegetable oil, but are not limited thereto. More preferably, the suitable carrier may be an isotonic solution, such as Hank's solution, Ringer's solution, phosphate buffered saline (PBS) containing triethanol amine) or sterilized water for injection, 10% ethanol, 40% propylene glycol, and 5% dextrose. To protect the injection against microbial contamination, the injection may further contain various antimicrobial and antifungal agents, such as paraben, chlorobutanol, phenol, sorbic acid, and thimerosal. In most cases, the injection may further contain an isotonic agent, such as sugar or sodium chloride.

The form of the transdermal administration preparation includes ointment, cream, lotion, gel, solution for external application, plaster, liniment, and aerosol. The "transdermal administration" means locally administering a pharmaceutical composition to skin to deliver an effective amount of an active ingredient through the skin. For example, the pharmaceutical composition of the present invention may be prepared into an injection formulation, which is then administered by slight pricking of the skin using a 30-gauge needle or direct application to the skin. These formulations are described in the literature, which is a formulary generally known in pharmaceutical chemistry (Remington's Pharmaceutical Science, 15th Edition, 1975, Mack Publishing Company, Easton, Pa.).

In the case of an inhalation agent, the compound used according to the invention may be conveniently delivered in the form of aerosol spray from a pressurized pack or a nebulizer, using a suitable propellant, for example, dichlorofluoromethane, trichlorofluoromethane, dichlorotetrafluoroethane, carbon dioxide, or other suitable gases. As for a pressurized aerosol, the dose unit may be determined by providing a valve that delivers a metered amount. For example, a gelatin capsule and a cartridge used in an inhaler or an insufflator may be formulated to contain a powder mixture of a compound and a suitable powder base material, such as lactose or starch.

Other pharmaceutically acceptable carriers may be referenced in the following literature (Remington's Pharmaceutical Sciences, 19th ed., Mack Publishing Company, Easton, Pa., 1995).

The pharmaceutical composition according to the present invention may further contain at least one buffer (for example, saline solution or PBS), a carbohydrate (for example, glucose, mannose, sucrose, or dextran), an anti-oxidant, a bacteriostat, a chelating agent (for example, EDTA or glutathione), an adjuvant (for example, aluminum hydroxide), a suspending agent, a thickener, and/or a preservative).

The pharmaceutical composition of the present invention may also be formulated by a method known in the art so as to provide rapid, continuous, or delayed release of an active ingredient after administration to a mammal.

In addition, the pharmaceutical composition of the present invention may be administered in combination with a known compound having an effect of preventing or treating an inflammatory disease, cancer and metastasis of cancer, diabetes, atherosclerosis, or cardiovascular disorder.

The present invention provides use of the peptide comprising SEQ ID NO: 1 for preparing an agent for treating an inflammatory disease.

Furthermore, the present invention provides a method for treating an inflammatory disease in a subject in need thereof, the method comprising administering the peptide comprising SEQ ID NO: 1 to the subject in an amount effective for treating the inflammatory disease in the subject.

The present invention provides use of peptide comprising SEQ ID NO: 1 for preparing an agent for anti-cancer and anti-metastasis.

Furthermore, the present invention provides a method for anti-cancer and anti-metastasis in a subject in need thereof, the method comprising administering the peptide comprising SEQ ID NO: 1 to the subject in an amount effective for anti-cancer and anti-metastasis in the subject.

The present invention provides use of the peptide comprising SEQ ID NO: 1 for preparing an agent for treating diabetes.

Furthermore, the present invention provides a method for treating diabetes in a subject in need thereof, the method comprising administering the peptide comprising SEQ ID NO: 1 to the subject in an amount effective for treating diabetes in the subject.

The present invention provides use of the peptide including SEQ ID NO: 1 for preparing an agent for treating atherosclerosis or a cardiovascular disorder.

Furthermore, the present invention provides a method for treating atherosclerosis or a cardiovascular disorder in a subject in need thereof, the method comprising administering the peptide comprising SEQ ID NO: 1 to the subject in an amount effective for treating atherosclerosis or a cardiovascular disorder in the subject.

The present invention provides use of the peptide comprising SEQ ID NO: 1 for preparing an agent for treating a heart failure.

Furthermore, the present invention provides a method for treating a heart failure in a subject in need thereof, the method comprising administering the peptide comprising SEQ ID NO: 1 to the subject in an amount effective for treating a heart failure in the subject.

As used herein, the term "effective amount" refers to an amount showing an effect of alleviating, treating, preventing, detecting, or diagnosing an inflammatory disease, cancer, diabetes, atherosclerosis, or cardiovascular disorder, or an effect of suppressing or reducing the condition of such diseases upon the administration to a subject. The "subject" may be an animal, preferably an animal including a mammal, especially a human being, and may be cells, tissues, organs, and the like derived from an animal. The subject may be a patient in need of the effect.

As used herein, the term "treating" or "treatment" refers collectively to alleviating symptoms caused by an inflammatory disease, cancer, diabetes, atherosclerosis, or cardiovascular disorder. Such term may include curing, substantially preventing, or improving the condition of such a disease, while including alleviating, curing, or preventing one symptom or most of symptoms resulting from such a disease, but is not limited thereto.

As used herein, the term "comprising" is used synonymously with "containing" or "being characterized", and does not exclude additional components or steps that are not mentioned in compositions or methods. The term "consisting of" means excluding additional elements, steps, or ingredients not otherwise specified. The term "consisting essentially of" means including the mentioned elements or steps as well as any element or step that does not substantially affect basic characteristics thereof in compositions or methods.

Advantageous Effects

Therefore, the present invention provides a polypeptide derived from CAP1 and a pharmaceutical composition comprising the polypeptide as an active ingredient. The method according to the present invention has effects of inhibiting the binding of resistin and CAP1, inhibiting NF-κB activity, and activating AMPK, and thus can be favorably used for the purpose of treating an inflammatory disease, cancer, diabetes, atherosclerosis, hyperlipidemia, a cardiovascular disease, and the like, which are caused by resistin activation, NF-κB activation, or AMPK inhibition.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

MODE FOR CARRYING OUT THE INVENTION

Hereinafter, the present invention will be described in detail.

However, the following examples are merely for illustrating the present invention and are not intended to limit the scope of the present invention.

<Methods>

Peptide Synthesis

Figure 1:
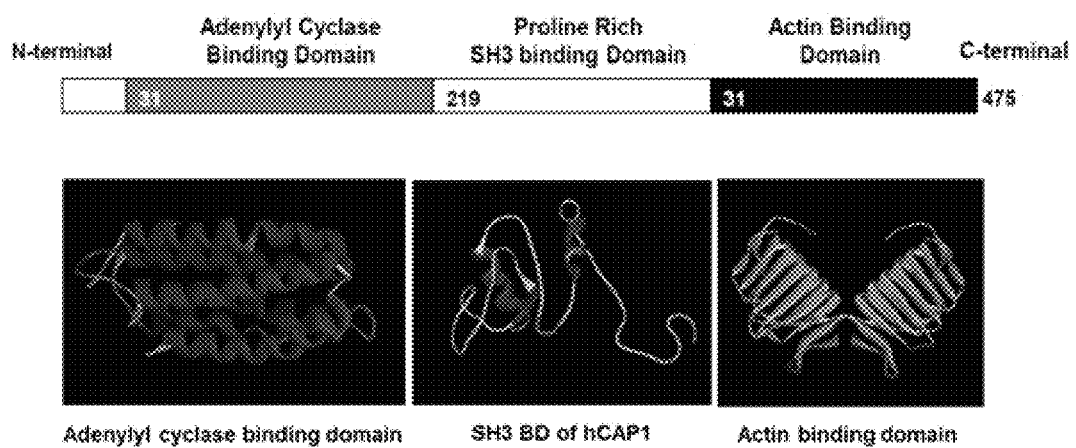
FIG. 1 shows a peptide comprising SEQ ID NO: 1 derived from SH3 domain in CAP1.
Figure 1:
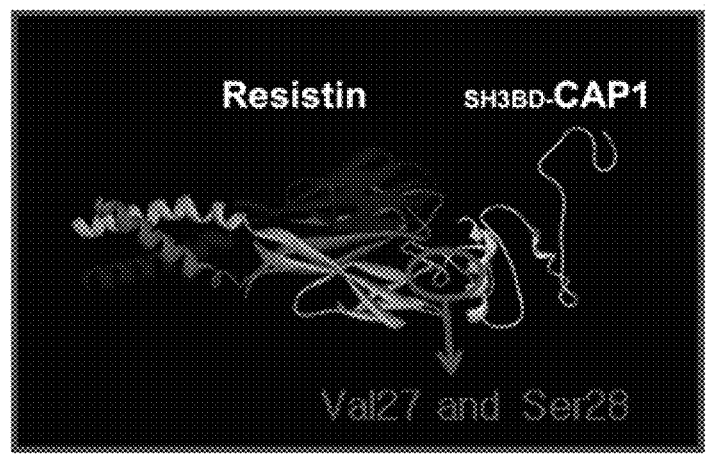

In the present invention, to develop a peptide that disturbs the binding of resistin and CAP1, VS_peptide (SEQ ID NO: 2) containing proline, Val 27, and Ser 28 in the SH3 domain of CAP1 (see FIG. 1) was synthesized (Peptron, Korea). To identify a site of the peptide of SEQ ID NO: 1, which is thought to be capable of inhibiting the interaction of resistin and CAP1, a total of six types of peptides (see SEQ ID NOS: 2 to 7, Table 1) were synthesized by substituting a proline-rich region and a site including valine at position 27 (Val 27) and serine at position 28 (Ser, 28) in the peptide corresponding to SEQ ID NO: 2 with alanine (A) (Peptron, Korea).

TABLE 1

| Name | Peptide sequence | Explanation | SEQ ID NO. |
| --- | --- | --- | --- |
| pep10 | GPPPPPVSTS | Shortened peptide based on VS and proline rich-1 | 1 |
| VS | PPPPGPPPPP VSTSSGSDES | Existing peptide | 2 |
| AA | PPPPGPPPPP AATSSGSDES | VS replaced with AA | 3 |
| pro1A | AAAAGPPPPP VSTSSGSDES | Proline rich-1 region replaced with A | 4 |
| pro2A | PPPPGAAAAA VSTSSGSDES | Proline rich-2 region replaced with A | 5 |
| AAA | AAAAGAAAAA AATSSGSDES | Proline rich regions and VS replaced with A | 6 |
| PVS | PVS | Peptide of three amino acids which are theoretically sufficient | 7 |

Animal Cell Lines and Incubation Thereof

In the experiments of the present invention, THP-1 (ATCC TIP-202, *Homo sapiens*, Human), MDA-MB-231 (ATCC HTB-26, *Homo sapiens*, Human), and 293F cell lines were used. The incubation conditions of the animal cell lines used in the present invention were determined by using cell line incubation methods from the American Type Culture Collection (ATCC), which is a distributing agency of each cell line. RPMI-1640 medium was used for THP-1, and DMEM medium was used for MDA-MB-231. The incubation methods of respective cell lines are as follows (the detailed incubation conditions may depend on the purpose). THP-1 cell lines were incubated in RPMI-1640 medium containing 1× antibiotic-antimycotic (Gibco, 15240-062) and 10% fatal bovine serum (FBS) in an incubator maintained at a temperature of 37° C. and a $CO_2$ partial pressure of 5%. MDA-MB-231 cell lines were incubated in a medium containing 100 units/ml penicillin and 100 ug/ml streptomycin at pH of 7.4 in an incubator maintained at a temperature of 37° C. and a $CO_2$ partial pressure of 5%.

Pull Down Assay

THP-1 cells were lysed with lysis buffer (20 mM Tris pH 7.5, 150 mM NaCl, 1% Triton X-100, 0.25% sodium deoxycholate, 1 mM EDTA, 1 Mm NaF, 1 mM $Na_3VO_4$, and protease inhibitor cocktail) to extract proteins. mFc-hResistin (0.5 ug) protein and VS_peptide (SEQ ID NO: 2) at 10 μM, 100 μM, and 500 μM were added to the extracted THP-1 protein (500 μg), followed by incubation at 4° C. overnight. mFC beads (20 μl) were added, and the protein complexes were pulled down at 4° C. for 3 hours, and then washed three times with lysis buffer. Then, SDS-PAGE sample buffer containing β-mercaptoethanol was added, followed by boiling at 100° C. for 5 minutes, and then a supernatant was obtained through centrifugation. It was investigated by western blotting using the hCAP1 antibody and mFc-HRP antibody whether the binding of hCAP1 and mFc-hResistin was inhibited by VS_peptide.

Immunoprecipitation

THP-1 cells were treated with resistin or resistin and a peptide for 12 hours, and then lysed with lysis buffer (20 mM Tris pH 7.5, 150 mM NaCl, 1% Triton X-100, 0.25% sodium deoxycholate, 1 mM EDTA, 1mM NaF, 1mM $Na_3VO_4$, and protease inhibitor cocktail). The resistin antibody or CAP1 antibody was added to the cell lysates, followed by immunoprecipitation at 4° C. for 3 hours. Mouse IgG was added for control. Protein A/G agarose beads were added to the THP-1 protein and CAP1 antibody complex, followed by incubation, and then through centrifugation, only beads were left and the supernatant was removed. Thereafter, the proteins bound to beads were separated by SDS-PAGE, and after electrophoresis, the gel was transferred onto the polyvinylidene fluoride (PVDF, Millipore), and then blocked with 5% skim milk at room temperature for 30 minutes. The blocked membrane was incubated with the anti-CAP1 antibody (SantaCruz Biotechnology, sc-100917) and the anti-resistin antibody (SantaCruz Biotechnology, sc-17575) as primary antibodies at room temperature for two hours or at 4° C. overnight according to the experiment, washed three times with a buffer for 5 minutes each, and again treated with the anti-mouse (SantaCruz Biotechnology, sc-2005) or anti-goat (SantaCruz Biotechnology, sc-2020) antibody as a secondary antibody at room temperature for one hour. After the incubation, the membrane was sufficiently washed at least three times for 10 minutes each, and bands were detected using ECL detection kit (Invitrogen, WP20005), and then analyzed.

Competitive ELISA Assay

Each well of a 96-well plate were coated with hCAP1 protein at a concentration of 2.5 μg/ml for 12 hours (overnight) at room temperature. Each well was washed two times with phosphate buffered saline (PBS, pH7.4). Each well was blocked with a blocking buffer containing 3% BAS at room temperature for 1 hour. The blocking buffer containing 3% BSA was mixed with 5 ug/ml mFc-hResistin protein and VS_peptide [SEQ ID NO: 2] at various concentrations (10 uM, 30 uM, 100 uM), followed by pre-incubation at room temperature for 1 hour. After the blocking solution was removed from the 96-well plate, 100 μl of the pre-incubated mixture of mFc-hResistin protein and VS_peptide (SEQ ID NO: 2) was dispensed in each well, followed by incubation at room temperature for 2 hours. Upon the completion of the incubation, each well was washed two times with PBS. After the anti-mouse-Fc-HRP antibody was diluted in a blocking buffer containing 3% BSA at 1:1000, 100 μl of the diluted antibody was dispensed in each well, followed by incubation at room temperature for 1 hour. Upon the completion of the incubation, each well was washed two times with PBS. After 100 μl of 3,3',5,5'-tetramethylbenzidine (TMB) substrate solution was dispensed in each well, and the incubation was conducted at room temperature for 20 minutes. After 100 μl of a stop solution was dispensed in each well, and the absorbance was measured at 450 nm using an ELISA reader.

Protein Binding Analysis (Surface Plasmon Resonance Analysis: SPR)

To measure the direct binding of hResistin and VS_peptide (SEQ ID NO: 2), SPR analysis was performed using Reichert SR7500DC system. hResistin (1.8 ug) and hPCSK9 (1.6 ug) proteins were immobilized on the carboxymethyl dextran hydrogel surface sensor chip (CMDH chip, Cat#: 13206066) by using a 10 mM sodium acetate immobilization buffer (pH 5.5 or pH 4.5). VS_peptide (SEQ ID NO: 2) diluted in PBS buffer (pH 7.4) in a dose-dependent manner was injected into the sensor chip (flow rate: 30 μl/min, association time: 3 min) to measure the response unit (RU) for binding strength. After the measurement of RU values for binding strength, PBS buffer (pH 7.4) was allowed to flow over the sensor chip at a rate of 30 μl/min for 3 minutes to measure dissociation RU values of VS_peptide (SEQ ID NO: 2) from hResistin immobilized on the chip. The dissociation equilibrium constant ($K_D$) of VS_peptide (SEQ ID NO: 2) for hResistin was derived using Scrubber2 software ($K_D=K_d/K_a$, $K_a$=association rate, $K_d$=dissociation rate).

Cell Migration Analysis

MDA-MB-231 cells were suspended in DMEM medium (0.1% FBS), and then the suspension was added at a concentration of $1×10^5$ cell/ml per well to uniformly spread throughout the upper chamber of 6-well Transwell. In the lower chamber, each of 50 μM VS_peptide (SEQ ID NO: 2) and AA_peptide (SEQ ID NO: 3) was mixed with DMEM medium (0.1% FBS), and resistin was added at 100 ng/ml. Thereafter, the cells were incubated in an incubator at 37° C. in 5% $CO_2$ for 24 hours. The cells penetrating the Transwell were stained using Crystal violet staining, and then quantified using the Image J program.

Binding of Albumin and Peptide Having Terminal Modified With Azide ($N_3$)

An azide ($N_3$) functional group was introduced into the amino terminal of VS_peptide (SEQ ID NO: 2), followed by a click reaction with ADIBO functional group-introduced albumin, thereby obtaining complexes. The peptide was introduced with 5 mg of albumin, followed by separation through a centrifugal filter (10 kDa). Here, albumin into which about eight surface ADIBO functional groups were introduced through 1:10 reaction was used, and the reaction time was 2 hours, and stirring was conducted in a dark room controlled at a temperature of 4° C. The final complex was identified by the reduction or deletion of particular peaks at 309 nm due to the UV masking of the ADIBO functional groups actually attached on albumin.

Radioisotope Labeling of Peptides by Using $N_3$-Chelating Reagents

The Cu-64, HCl solution was dried by blowing high-purity nitrogen (99.999%) while HCl was vaporized in the Cu-64 radioisotope solution present in HCl solution. After the pH was adjusted to 5 using 200 µl of 1 M sodium acetate with pH 5.3, a 10 nmol NOTA-$N_3$ solution (less than 10 µl) was added, followed by reaction at 37° C. for 20 minutes, and then it was confirmed that all of the radioactive isotopes were chelated to NOTA-$N_3$ through thin layer chromatography in 0.1 M citrate and 0.1 M sodium carbonate solutions.

PET Image Acquisition and Biodistribution Analysis

VS_peptide and albumin-conjugated VS_peptide were injected at 36-40 µCi per mouse into the tail vein of C57BL/6 normal mice. After the injection, PET images were acquired at intervals of 0, 1, 2, 4, 24, and 48 hours using the GENISYS□ machine from Sofie Bioscience. After the image acquisition, pharmacokinetic data were obtained by monoexponential fitting using the image analysis program Amide.

Animal Models and Insulin Tolerance Test

Male mice aged 8-10 weeks were maintained at a 12-hour cycle (12-hour light/12-hour dark) with a free diet. All mice were fed with a high-fat diet (60% fat diet, TD-6414: Harlan) for 8 weeks. For six weeks after the high-fat diet, VS_peptide_albumin (SEQ ID NO: 2) (albumin-conjugated VS_peptide (SEQ ID NO: 2)) and AA_peptide (SEQ ID NO: 3) (albumin-conjugated AA_peptide (SEQ ID NO: 3)) each were administered at 10 mg/kg once every two days. For the insulin tolerance test (ITT), fasting was performed for 16 hours prior to abdominal administration. After the mice fasting for ITT were abdominally administered with insulin at 0.65 U/kg body weight, blood was collected from vein at 0, 15, 30, 60, and 120 minutes, and then blood glucose changes were measured using a glucometer (Accu-Chek Perfoma kit, Roche) and a glucose paper (Accu-Chek Perfoma Strip, Roche).

After the mice were anesthetized with Zoletil and Rompun, blood was collected from the heart, and serum was isolated from the blood and used for analysis. The mice were sacrificed and the liver was extracted. The extracted liver lobes were prepared into tissue slides (paraffin, O.C.T-freezing), and the rest were used for in vitro experiments. In addition, fat was extracted, and half thereof was made into tissue slides and the other half was used for in vitro experiments. All animal experiment methods and euthanasia were approved by the Institutional Animal Care and Use Committee (IACUC) of Seoul National University.

H&E Staining

Liver tissue was analyzed by H&E staining. Paraffin section slides were placed in xylene, and then rehydrated by washing with different concentrations of aqueous ethanol solutions. The liver tissue was stained with hematoxylin for 7 minutes, followed by Eosin staining for 3 seconds. The liver tissue slides were washed with distilled water in each step. All H&E staining procedures were performed using Autostainer XL (Leica).

Immunohistochemistry

The paraffin sectioned adipose tissues were placed in xylene (de-paraffin), and then washed with different concentrations of aqueous ethanol solutions After the adipose tissues were washed with running water, antigens were retrieved using an antigen retrieval solution (Dako, S2031) at 95° C. To identify infiltrated macrophages, the CD11b-specific antibody (eBioscience, MCA497, mouse anti-CD11b), the anti-mouse HRP-conjugated secondary antibody, and DAB solution of Vector Lab. were used. The stained tissues were observed by Olympus IX71 microscope, which is an Olympus DP50 camera module.

Real-Time PCR

After the liver and adipose tissues were rapidly cooled with LN2 and ground by a mortar, RNA was extracted from about 100 mg of each of the tissues (Qiagen, RNeasy plus Mini Kit). Then, 500 ug of RNA was synthesized into cDNA (Takara, Primescript 1st strand cDNA synthesis kit), and DNA amplification was measured by PCR (Applied Biosystems, 7500 Real-time PCR). mPEPCK, mG6Pase, mPGC1α, mACC, mFASN, and mSREBP-1, which are metabolic genes, were measured using cDNA synthesized from RNA extracted from the liver tissue, and mTNFα, mIL-6, mIL-1β, MCP-1, and CXCL-5, which are inflammatory cytokines, were measured using cDNA synthesized from RNA extracted from the adipose tissue. mGAPDH was used as internal control, and the measurement values were normalized.

Statistical Analysis

Quantitative graphs were obtained by counting infiltrated cells per crown-like structure of adipocytes, and statistical analysis was performed using GraphPad Prism 5 software.

EXAMPLE 1

Peptide Inhibiting Binding of Resistin and CAP1

<1-1> Confirmation on Inhibitory Activity of Peptide Through SPR System

To verify that VS_peptide (SEQ ID NO: 2) competitively inhibits the binding with CAP1 by binding resistin, the direct binding of resistin and VS_peptide (SEQ ID NO: 2) was analyzed by SPR system. The resistin protein was immobilized on the censor chip, and VS_peptide (SEQ ID NO: 2) was allowed to flow over the sensor chip at a rate of 30 µl/min for 3 minutes to obtain the dissociation equilibrium constant ($K_D$).

Figure 2:
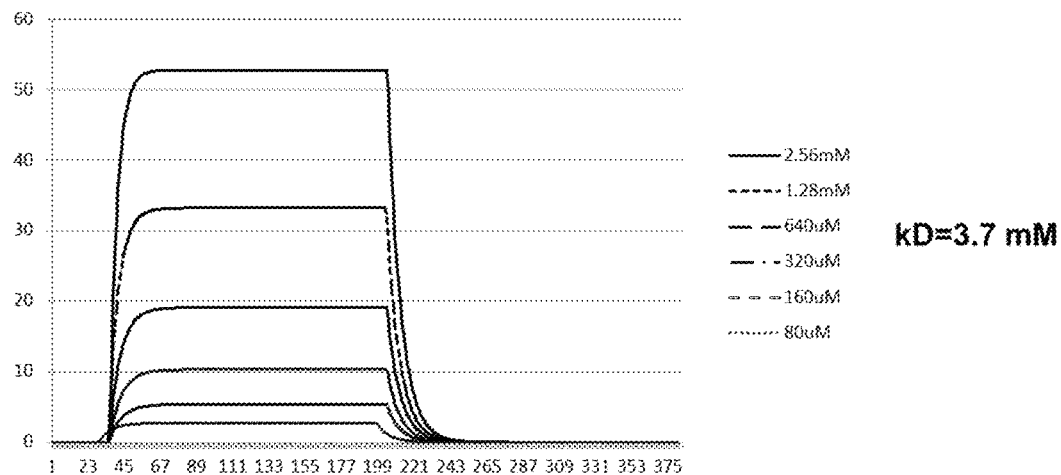
FIG. 2 is a graph showing the binding of resistin and VS_peptide (SEQ ID NO: 2) derived from the SH3 domain of CAP1, which was measured by surface plasmon resonance (SPR) systems.

As a result, as shown in FIG. 2, dose-dependent binding curves are shown in FIG. 2 ($K_D$=3.7 mM). It can be seen through these results that VS_peptide (SEQ ID NO: 2) effectively binds with resistin.

<1-2> Confirmation on Inhibitory Activity of Peptide Through Pull Down Assay

To investigate the effect of VS_peptide [SEQ ID NO: 2], which was synthesized by containing proline, Val 27, and Ser 28, in the SH3 domain of CAP1, on the direct binding of resistin and CAP1, pull down assay was performed.

Specifically, THP-1 cell lysates were treated with 1 µg/ml of mFC-hResistin, treated with VS_peptide (SEQ ID NO: 2) at 10 µM, 100 µM, and 500 µM each, and then pulled down using Fc beads. The proteins bound to beads were separated by SDS-PAGE, and subjected to western blotting using the CAP1 antibody.

Figure 3:
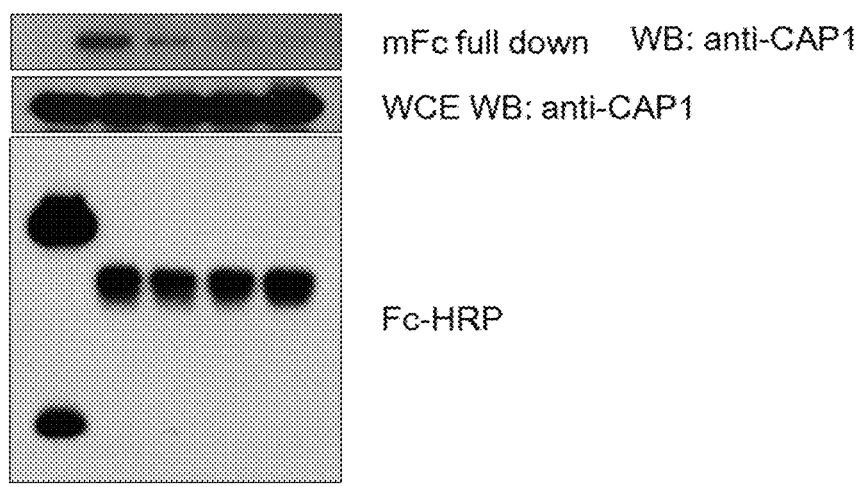
FIG. 3 illustrates that VS_peptide (SEQ ID NO: 2) inhibited the binding of CAP1 and resistin in a dose-dependent manner, and shows the results, wherein the Fc-fused recombinant resistin protein and the peptide at various concentrations as shown in the drawing were added to THP-1 cell lysates, and the protein complexes were pulled down using Fc beads, and subjected to western blotting (In vitro pull-down assay).

As a result, as shown in FIG. 3, it could be confirmed that the amount of CAP1 binding to resistin was reduced when VS_peptide (SEQ ID NO: 2) was added. It could be confirmed that the higher the concentration of the added peptide, the more the binding of resistin and CAP1 is inhibited.

<1-3> Confirmation on Inhibitory Activity of Peptide Through Immunoprecipitation To investigate the effect of VS_peptide [SEQ ID NO: 2] on the binding of resistin and CAP1 in cells, the immunoprecipitation was performed according to the above experimental method.

After THP-1 cells were treated with resistin or resistin and the peptide for 12 hours, the cells were lysed. The cell lysates were immunoprecipitated at 4° C. for 3 hours after the addition of the resistin antibody or CAP1 antibody, and mouse IgG was added for control. The produced immunocomplexes were collected by incubation with protein G-agarose (Roche Applied Science) at 4° C. for 1 hour. After washing, the immunoprecipitated proteins were subject to western blotting using the anti-CAP1 antibody or anti-resistin antibody.

Figure 4:
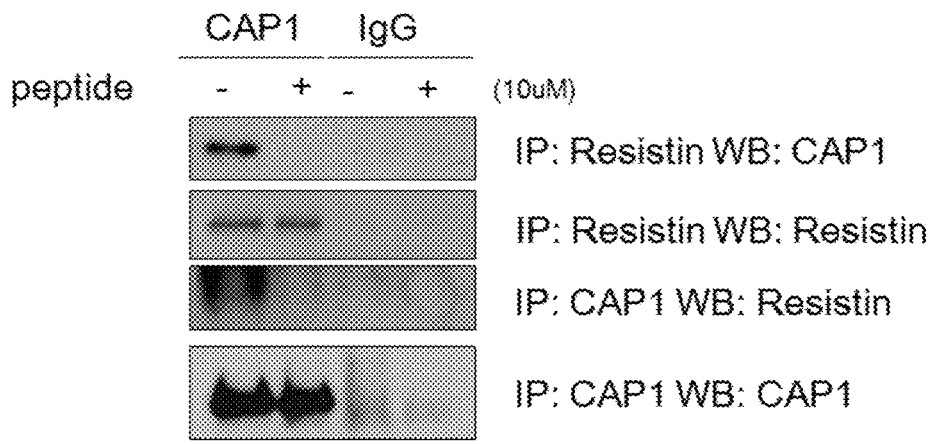
FIG. 4 shows the results, wherein to investigate whether VS_peptide (SEQ ID NO: 2) inhibits the binding of resistin and CAP1, THP-1 cells were lysed without or without the treatment with the peptide, and the cell lysates were immunoprecipitated with each resistin antibody and the CAP1 antibody, and subjected to western blotting using the CAP1 antibody and resistin antibody.

As shown in FIG. 4, the treatment with VS_peptide (SEQ ID NO: 2) showed no bands in the case where precipitation with resistin and western blotting with CAP1 were carried out and in the case were immunoprecipitation with CAP1 and western blotting with resistin were carried out. It can be seen through these results that the VS_peptide (SEQ ID NO: 2) effectively inhibits the binding of resistin and CAP1.

<1-4> Confirmation on Inhibitory Activity of Peptide Through Competitive ELISA

To investigate the effect of VS_peptide (SEQ ID NO: 2) on the binding of resistin and CAP1, competitive ELISA was performed.

Each well of a 96-well plate was coated with rhCAP1, and incubated with various concentrations of VS_peptide (SEQ ID NO: 2) and mFC-hResistin recombinant protein, followed by washing, thereby binding CAP1 and resistin. The resistin bound to the HRP-conjugated mFc antibody was measured by ELISA at an absorbance of 450 nm.

Figure 5:
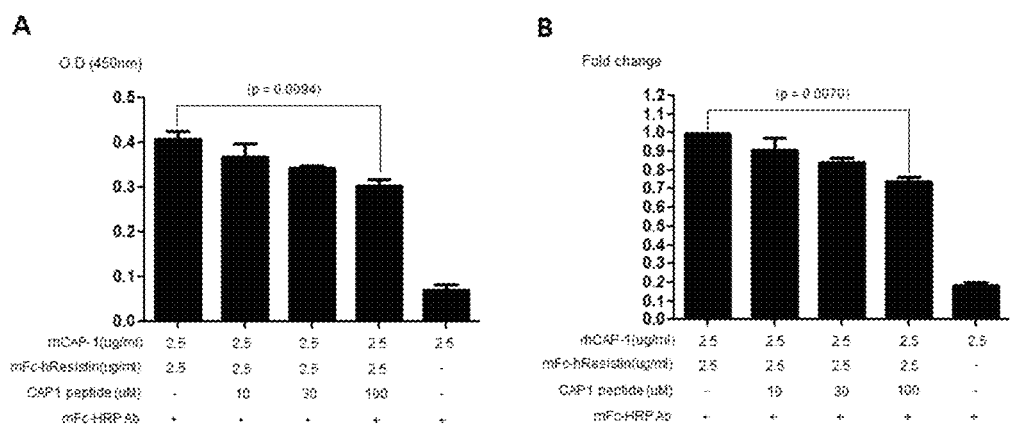
FIG. 5 shows the results, wherein mFc-fused recombinant resistin protein and VS_peptide (SEQ ID NO: 2) with various concentrations as shown in the drawing were added to a 96-well plate coated with recombinant CAP1 protein, and then to investigate whether VS_peptide (SEQ ID NO: 2) inhibits the binding of resistin and CAP1 in a dose-dependent manner, competitive ELISA was conducted.

As a result, as shown in FIG. 5, the OD value was decreased in the addition of VS_peptide (SEQ ID NO: 2) rather than the non-addition thereof, and the higher the concentration of the added peptide, the smaller the OD value. It can be confirmed that the treatment with the peptide at a concentration of 100 μM showed an inhibitory effect of about 25%. It can be seen through these results that the VS_peptide (SEQ ID NO: 2) inhibits the binding of resistin and CAP1.

EXAMPLE 2

Site of Peptide to Inhibit Binding of Resistin and CAP1

To investigate a core site of the VS_peptide (SEQ ID NO: 2) to inhibit the binding of resistin and CAP1, the peptides of SEQ ID NOS: 1 to 7 were synthesized as shown in Table 1, and pull down assay was performed using each of the peptides.

THP-1 cell lysates were treated with mFC-hResistin (1 μg/ml) and each of the peptides of SEQ ID NOS: 1 to 7 at 50 μM each, and pulled down using Fc beads. Thereafter, the proteins bound to Fc beads were separated by SDS-PAGE, and then subjected to western blotting using the CAP1 antibody.

Figure 6:
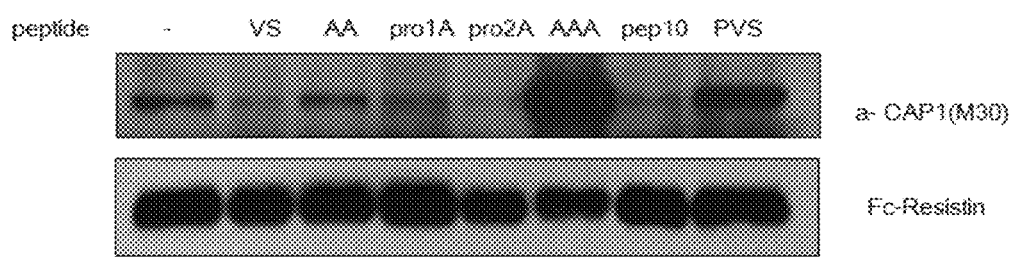
FIG. 6 shows the results of comparing CAP1-resistin binding inhibitory effects of the peptides of SEQ ID NOS: 1 to 7 through in vitro pull-down assay in FIG. 3. THP-1 cell lysates were mixed with Fc-fused recombinant resistin protein and each peptide as shown in the drawing, and then CAP1 bound to Fc beads via precipitation was measured by western blotting, thereby comparing the binding of resistin and CAP1 and the binding inhibitory effects of the respective peptides.

As a result, as shown in FIG. 6, the peptide of SEQ ID NO: 6, in which proline, valine (Val 27), and serine (Ser 28) are all substituted with alanine (A) (AAA), allowed the strongest binding of resistin and CAP1, and the peptide of SEQ ID NO 4 (pro1A), the peptide of SEQ ID NO: 5 (pro2A), and the peptide of SEQ ID NO: 1 (pep10) inhibited the binding of resistin and CAP1 at similar levels to the VS_peptide (SEQ ID NO: 2). The peptide of SEQ ID NO: 3 (AA) failed to inhibit the binding of resistin and CAP1 compared with the peptide VS. It can be seen through these results that the core site of the peptide to inhibit the binding of resistin and CAP1 includes Val 27 and Ser 28. In the subsequent experiments, the peptide of SEQ ID NO: 3, which has a similar sequence to VS_peptide (SEQ ID NO: 2) as soon as possible and does not show the binding inhibitory effect, was used as control.

EXAMPLE 3

Effect of Peptide Disturbing Binding of Resistin and CAP1 on NF-κB Activity

To investigate the effect of VS_peptide (SEQ ID NO: 2) on NF-κB activity, p65 phosphorylation was compared between the addition of VS_peptide (SEQ ID NO: 2) and the addition of AA_peptide (SEQ ID NO: 3). THP-1 cells were treated with resistin to activate NF-κB, and VS_peptide (SEQ ID NO: 2) and AA_peptide (SEQ ID NO: 3) were added, and then western blotting using the p-p65 antibody was performed for NF-κB activity.

Figure 7:
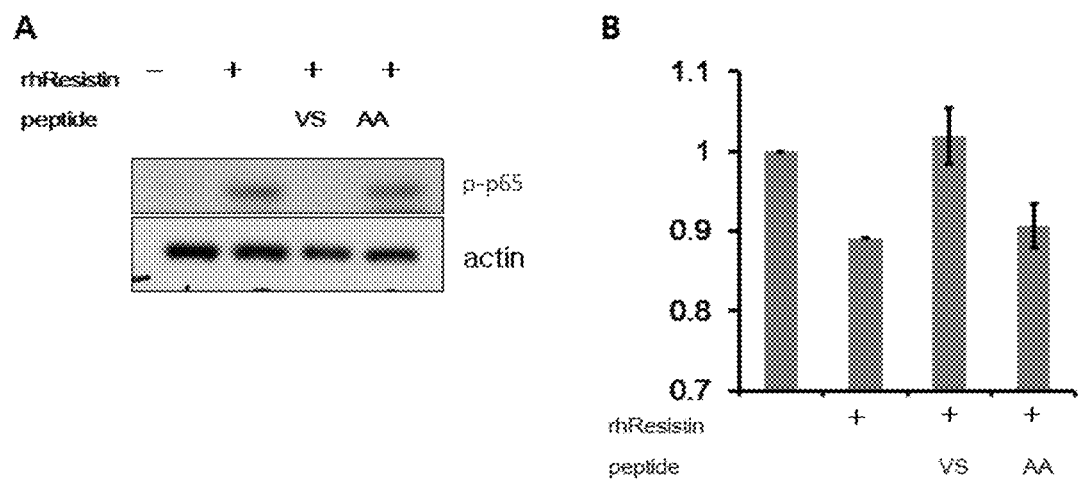
FIG. 7 shows that, to investigate the effect of VS_peptide (SEQ ID NO: 2) on NF-κB activity, THP-1 cells were treated with resistin to activate NF-κB, and the activity of NF-κB when VS_peptide (SEQ ID NO: 2) and AA_peptide (SEQ ID NO: 3) were expressed by measuring p65 phosphorylation (panel A: western blotting using the p-p65 antibody (top) and actin (bottom), panel B: quantitative values of p-p65 for actin in the results of panel A).

As a result, as shown in FIG. 7, p65 was phosphorylated by resistin treatment, and p65 phosphorylation was inhibited by the treatment with VS_peptide (SEQ ID NO: 2), and p65 phosphorylation was not inhibited by AA_peptide [SEQ ID ON: 3]. It can be seen through these results that VS_peptide inhibits p65 phosphorylation induced by resistin, but the inhibitory effect was lost by the peptide with AA substituted for VS, indicating that VS is an important site.

EXAMPLE 4

Effect of Peptide Disturbing Binding of Resistin and CAP1 on AMPK Activity

To investigate the effect of VS_peptide (SEQ ID NO: 2) on AMPK activity, AMPK phosphorylation was compared between the addition of VS_peptide (SEQ ID NO: 2) and the addition of AA_peptide (SEQ ID NO: 3). To investigate the effect of VS_peptide (SEQ ID NO: 2) on AMPK activity, HepG2 cells were treated with AICAR to activate AMPK and treated with resistin, and the cells were treated with VS_peptide (SEQ ID NO: 2) and AA_peptide (SEQ ID NO: 3) at 50 μM each. The western blotting was performed to investigate AMPK activity in HepG2 cells through the phosphorylation of AMPK, the phosphorylation of ACC, which is a substrate of AMPK, and the expression level of LDLR.

Figure 8:
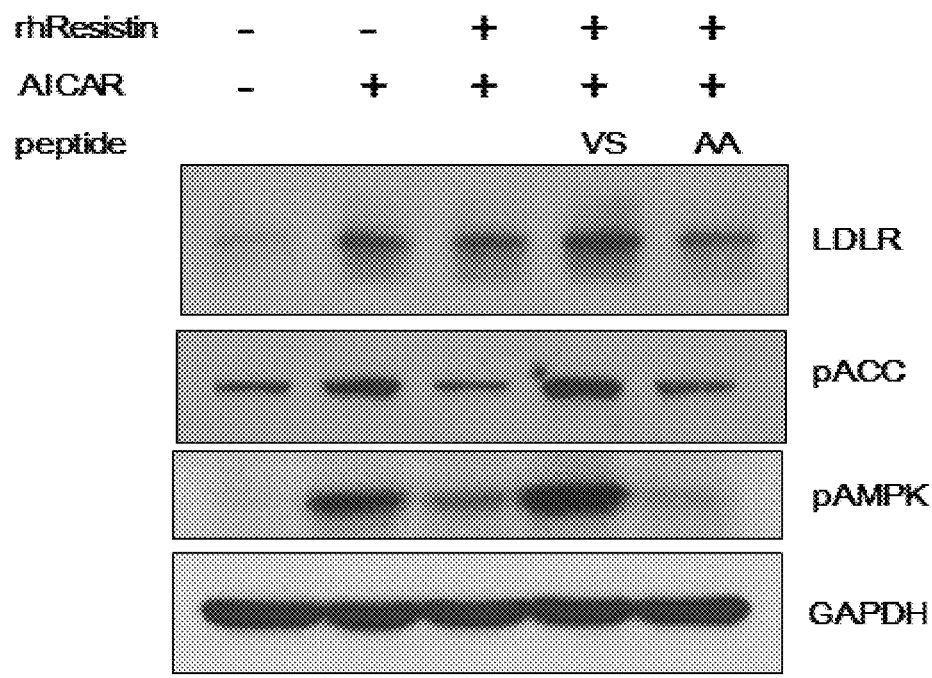
FIG. 8 shows that, to investigate the effect of VS_peptide (SEQ ID NO: 2) on AMPK activity, HepG2 cells were treated with AICAR to activate AMPK and treated with resistin, and the activity of AMPK when VS_peptide (SEQ ID NO: 2) and AA_peptide (SEQ ID NO: 3) were added was expressed by measuring the phosphorylation of AMPK, the phosphorylation of ACC, which is a substrate of AMPK, and the expression level of LDLR.

As a result, as shown in FIG. 8, the phosphorylation of AMPK and ACC and the expression level of LDLR were increased in the addition of VS_peptide (SEQ ID NO: 2) compared with the addition of only resistin. In addition, the phosphorylation of AMPK and ACC was not increased and the expression level of LDLR was similar in the addition of AA_peptide (SEQ ID NO: 3) compared with the addition of only resistin.

It can be seen through these results that VS_peptide (SEQ ID NO: 2) increases the phosphorylation of AMPK and ACC and increases LDLR.

EXAMPLE 5

Confirmation on Cancer Cell Migration Inhibitory Effect

To investigate the effect of the VS_peptide (SEQ ID NO: 2) of the present invention on the migration of cancer cells, cell migration analysis was performed using breast cancer cell lines according to the above experimental method.

MDA-MB-231 cells were suspended in DMEM medium, and then placed in 24-well plates at a concentration of $1\times10^5$ cell/ml per well. After 50 ng/ml of resistin was placed in each well, VS_peptide (SEQ ID NO: 2) and AA_peptide (SEQ ID NO: 3) were placed at 30 µM and 50 µM, respectively. Thereafter, the cells were incubated in an incubator at 37° C. and 5% $CO_2$ for 6-15 hours. Thereafter, cell migration after 6 hours and 15 hours was observed using a microscope.

Figure 9:
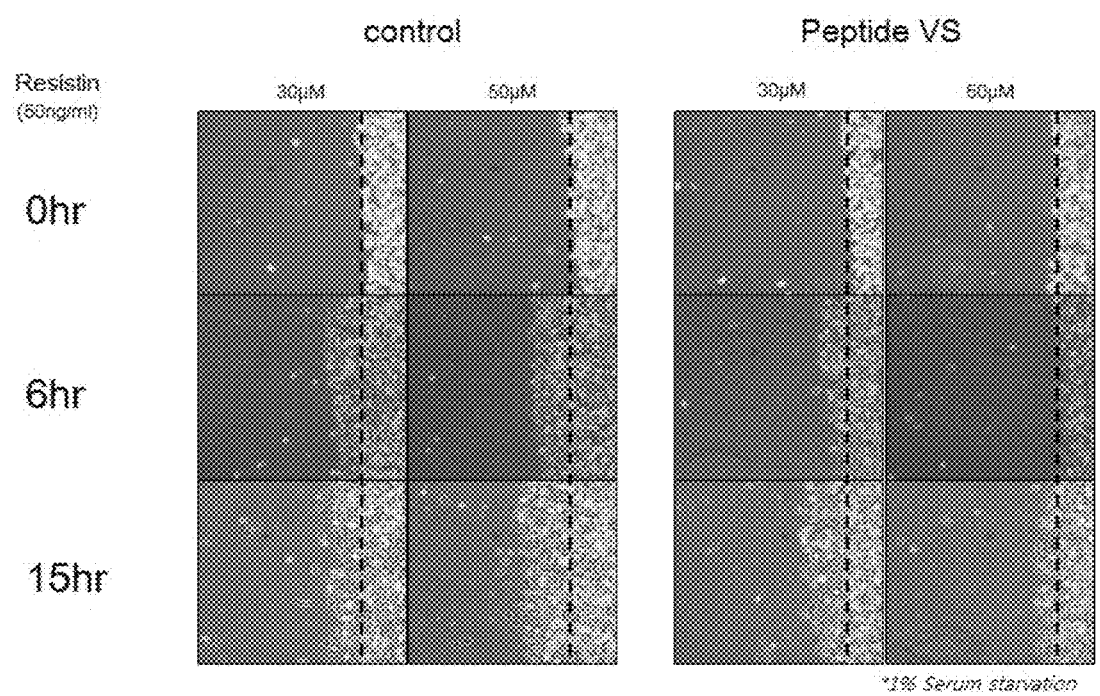
FIG. 9 shows the results, wherein to investigate the effect of VS_peptide (SEQ ID NO: 2) on the migration of cancer cells induced by resistin, MB231 cells (breast cancer cell line) were treated with VS_peptide (SEQ ID NO: 2) and AA_peptide (SEQ ID NO: 3), followed by cell migration experiments.

As a result, as shown in FIG. 9, the amount of cell migration was smaller in the addition of VS_peptide (SEQ ID NO: 2) rather than the addition of AA_peptide (SEQ ID NO: 3), and the amount of cell migration was smaller in 30 µM rather than 50 µM. Therefore, it can be seen that VS_peptide (SEQ ID NO: 2) inhibits the migration of cancer cells.

EXAMPLE 6

Measurement of Peptide Pharmacokinetics

To increase drug delivery efficiency and drug effect duration of VS_peptide (SEQ ID NO: 2), albumin was bound to the peptide. VS_peptide (SEQ ID NO: 2) and albumin-conjugated VS_peptide (SEQ ID NO: 2) were labeled with a radioisotope, and then injected at 36-40 uCi each into the tail vein of male mice aged 8 weeks. PET images were acquired at intervals of 0, 1, 2, 4, 24, and 48 hours, and kinetics of the peptide in the body were observed.

Figure 10:
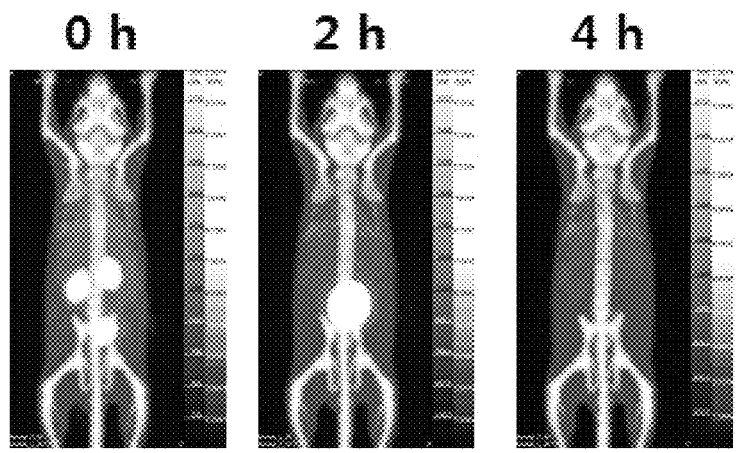
FIG. 10 shows the results, wherein albumin was conjugated to VS_peptide (SEQ ID NO: 2) to increase the in vivo absorption and half-life of VS_peptide (SEQ ID NO: 2), and pharmacokinetic experiments were conducted by administering mice with a peptide medicine (A) and an albumin-conjugated medicine (B) to measure pharmacokinetics.
Figure 10:
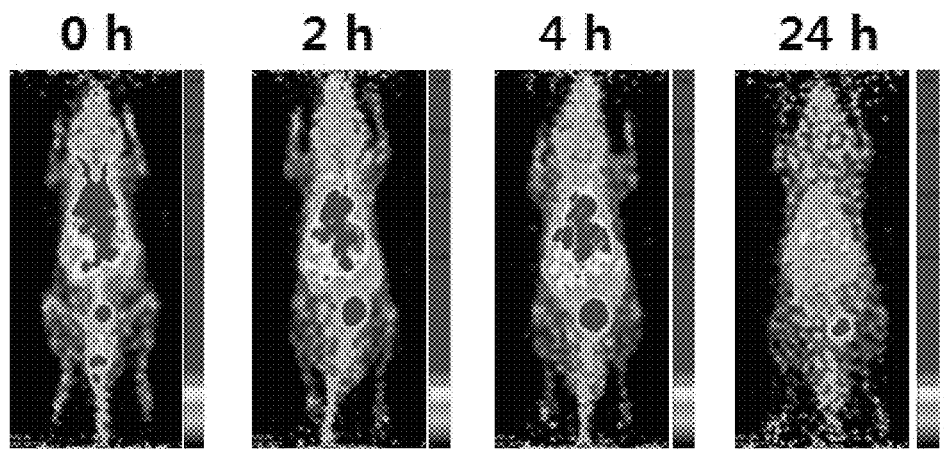

As a result, as show in FIG. 10, the peptide medicine administered was observed to be removed in the body within 4 hours. Whereas, the albumin-conjugated peptide medicine administered remained in the body after 24 hours and remained in the body within up to 30-35 hours.

It can be seen through these results that the albumin-conjugated peptide medicine remains longer and thus is more suitable as a medicine than the peptide medicine.

EXAMPLE 7

Confirmation on In Vivo Effect of Peptide

Figure 11:
FIG. 11 is a schematic diagraph showing an experimental procedure to investigate the effects of peptides in mouse models. After obesity was induced in 8-week old mice by a high-fat diet for 8 weeks, albumin-conjugated VS_peptide (SEQ ID NO: 2) was intravenously injected for 4 weeks to investigate the effects thereof. Summary of animal experiments for FIGS. 12 to 18 is shown.

To investigate the effect of the peptide shown in the body, experiments were carried out according to the above experimental method, as shown in the schematic diagram of FIG. 11.

<7-1> Effect of Peptide on Body Weight in CAP1-Deficient Mice

To induce a metabolic disease in 8-week old male CAP1+/− mice, the mice were fed with a high-fat diet for 8 weeks according to the above experimental method. After the high-fat diet for 8 weeks, VS_peptide_albumin (SEQ ID NO: 2) and AA_peptide_albumin (SEQ ID NO: 3) were intravenously administered everyday for 6 weeks, and body weight changes were measured.

Figure 12:
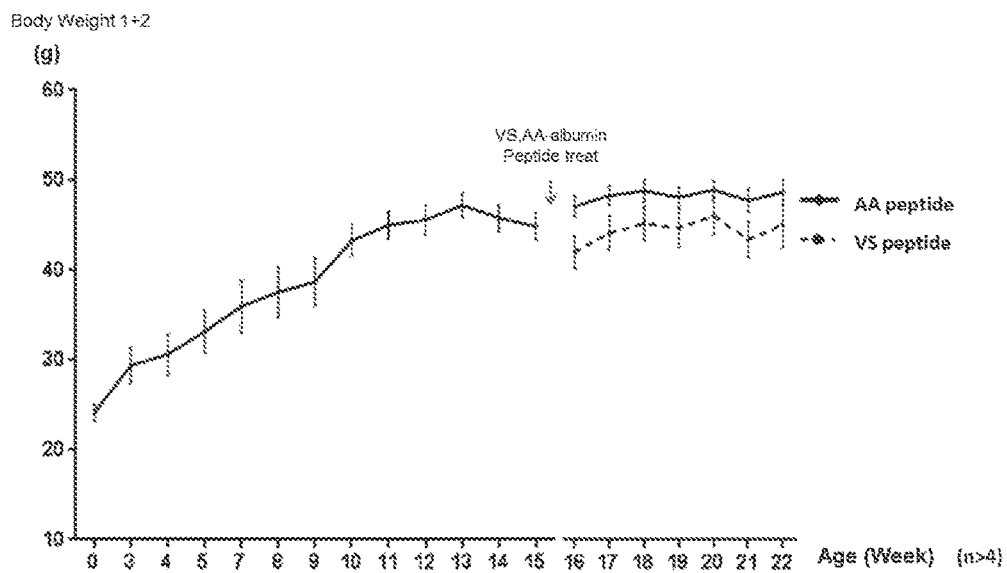
FIG. 12 shows the results, wherein to investigate the effect of VS_peptide (SEQ ID NO: 2) on body weight, mice were intravenously injected with VS_peptide (SEQ ID NO: 2) and AA_peptide (SEQ ID NO: 3) to measure body weight changes.

As a result, as shown in FIG. 12, the body weight increase was smaller in the treatment with VS_peptide_albumin (SEQ ID NO: 2) rather than the treatment with AA_peptide_albumin [SEQ ID NO: 3].

<7-2> Effect of Peptide on Blood Glucose in CAP1-Deficient Mice

To induce a metabolic disease in 8-week old male CAP1+/− mice, the mice were fed with a high-fat diet for 8 weeks according to the above experimental method. After the high-fat diet for 8 weeks, VS_peptide_albumin (SEQ ID NO: 2) and AA_peptide_albumin (SEQ ID NO: 3) were intravenously administered everyday for 6 weeks. After the 6-week peptide administration, fasting mice were anesthetized and blood was collected from the heart. Serum was separated and blood glucose was measured.

Figure 13:
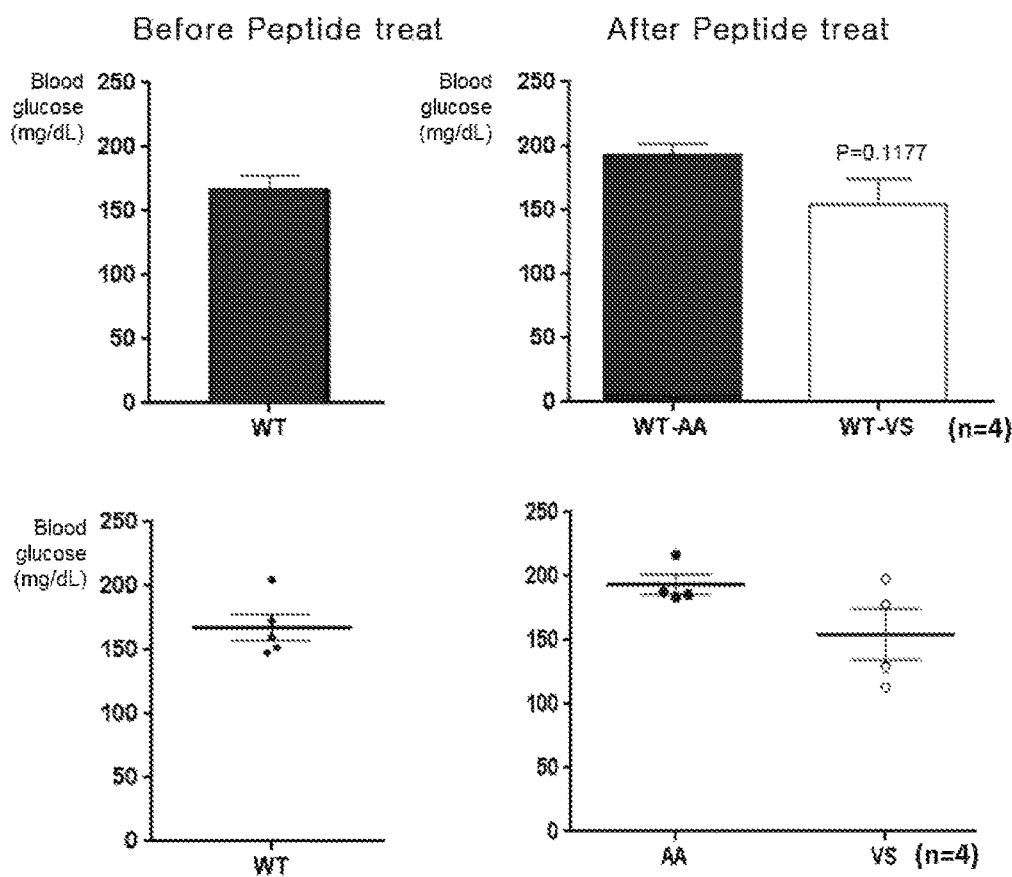
FIG. 13 shows the results, wherein to investigate the effect of VS_peptide (SEQ ID NO: 2) on blood glucose, mice were intravenously injected with VS_peptide (SEQ ID NO: 2) and AA_peptide (SEQ ID NO: 3) to measure fasting blood glucose.

As a result, as shown in FIG. 13, the blood glucose was slightly increased in the treatment with AA_peptide_albumin (SEQ ID NO: 3) compared with the pre-treatment with the peptide, and there was little difference between the treatment with VS_peptide_albumin (SEQ ID NO: 2) and the pre-treatment with the peptide.

<7-3> Effect of Peptide on Liver in CAP1-Deficient Mice

To induce a metabolic disease in 8-week old male CAP1+/− mice, the mice were fed with a high-fat diet for 8 weeks according to the above experimental method. After the high-fat diet for 8 weeks, VS_peptide_albumin (SEQ ID NO: 2) and AA_peptide_albumin (SEQ ID NO: 3) were intravenously administered everyday for 6 weeks. On the last day after the 6-week peptide administration, the mice were fasted for 16 hours and euthanized, and the liver was harvested therefrom. The harvested liver tissue was subjected to H&E staining, and observed at magnifications of ×100 and ×200.

Figure 14:
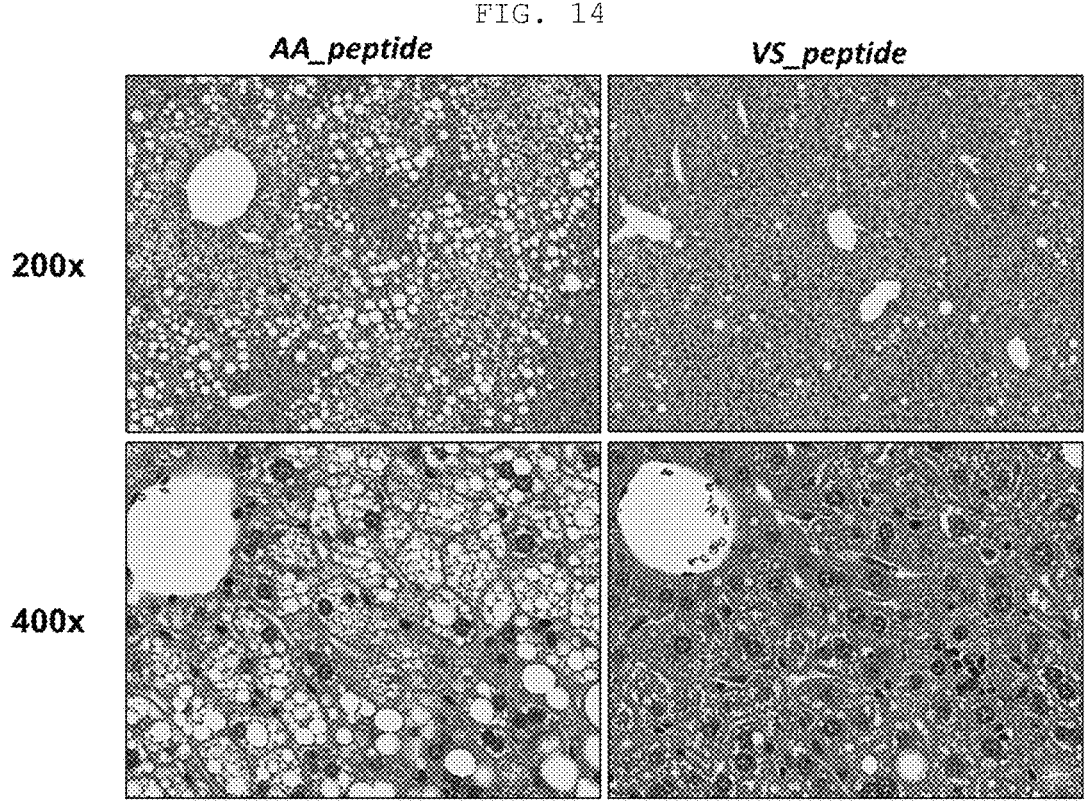
FIG. 14 shows the results, wherein to investigate the effect of VS_peptide (SEQ ID NO: 2) on liver, H&E staining experiments were conducted.

The results are shown in FIG. 14.

<7-4> Effect of Peptide on Adipocytes in CAP1-Deficient Mice

After 8-week old male CAP1+/− mice were fed with a high-fat diet for 8 weeks according to the above experimental method, VS_peptide_albumin (SEQ ID NO: 2) and AA_peptide_albumin (SEQ ID NO: 3) were intravenously administered everyday for 6 weeks. On the last day after the 6-week peptide administration, the mice were fasted for 16 hours and euthanized, and adipose tissues were harvested therefrom. The harvested adipose tissues were subjected to immunohistochemistry staining, and observed at magnifications of ×100 and ×200.

Figure 15:
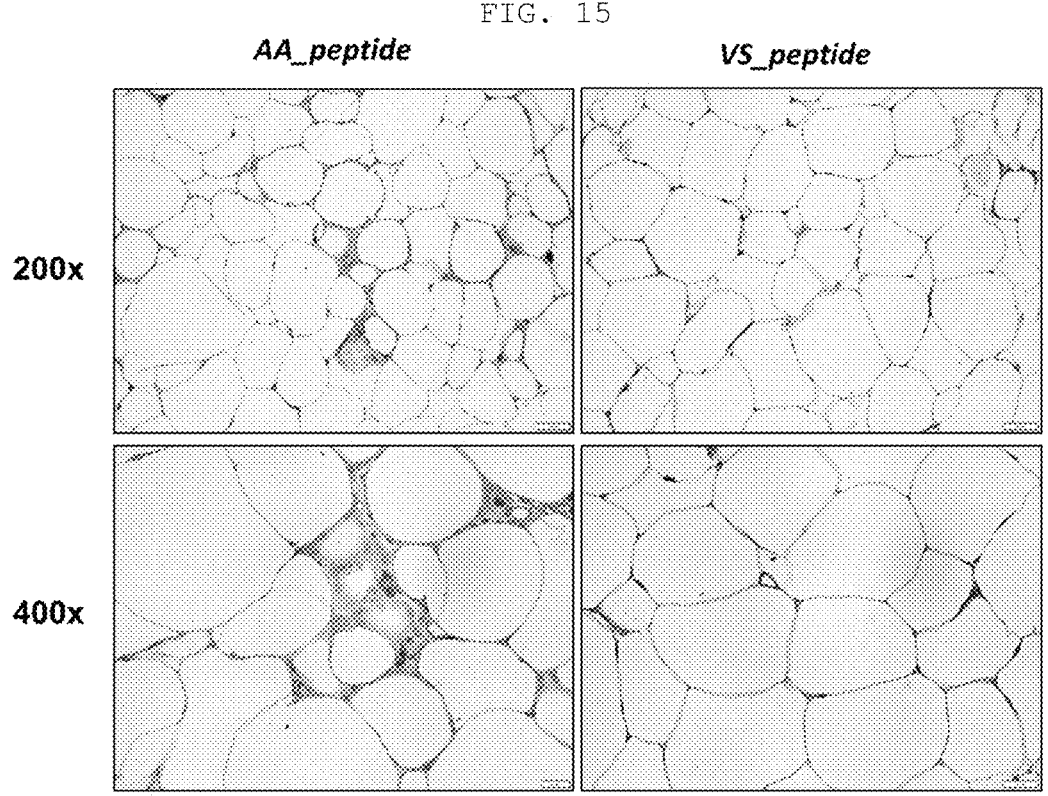
FIG. 15 shows the results, wherein to investigate the effect of VS_peptide (SEQ ID NO: 2) on chronic inflammation induced by obesity, the macrophages infiltrating into fat were subjected to immunohistochemistry staining experiments using the CD11b antibody.

The results are shown in FIG. 15.

<7-5> Effect of Peptide on In Vivo Insulin

After 8-week old male CAP1+/− mice were fed with a high-fat diet for 8 weeks according to the above experimental method, VS_peptide_albumin (SEQ ID NO: 2) and AA_peptide_albumin (SEQ ID NO: 3) were intravenously administered everyday for 6 weeks. On the last day, the mice were fasted for 16 hours and then intravenously injected with insulin. Thereafter, the blood was collected at 0, 15, 30, 60, and 120 minutes, and blood glucose changes were measured.

Figure 16:
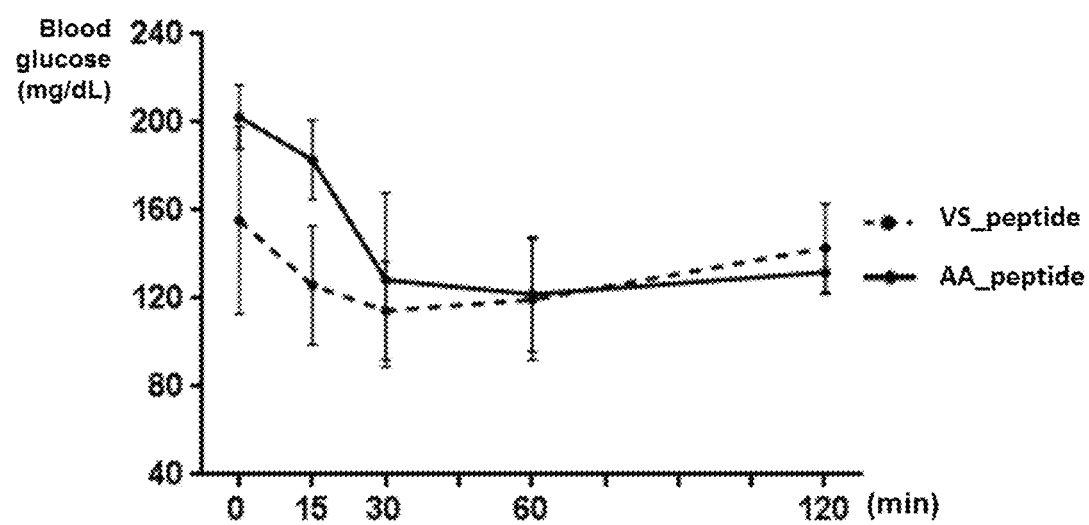
FIG. 16 is a graph showing the results, wherein to investigate the effect of VS_peptide (SEQ ID NO: 2) on insulin tolerance induced by obesity, the insulin tolerance test (ITT) was conducted.

As a result, as shown in FIG. 16, the VS_peptide_albumin (SEQ ID NO: 2) administration group showed low fasting blood glucose than the AA_peptide_albumin (SEQ ID NO: 3) administration group, and the blood glucose was significantly reduced at 15 minutes after insulin injection. It can be seen through these results that VS_peptide (SEQ ID NO: 2) has effects of lowering blood glucose and controlling insulin-mediated blood glucose control in the body.

EXAMPLE 8

Effect of Peptide on Expression of Metabolic Genes and Cytokine Genes

After 8-week old male CAP1+/− mice were fed with a high-fat diet for 8 weeks according to the above experimental method, VS_peptide_albumin (SEQ ID NO: 2) and AA_peptide_albumin (SEQ ID NO: 3) were intravenously administered everyday for 6 weeks. Then, the mice were sacrificed and RNA was extracted from liver and adipose tissues. Thereafter, the expression levels of mPEPCK, mG6Pase, mPGC1α, mACC, mFASN, and mSREBP-1, which are metabolic genes extracted from liver, were measured by real-time PCR, and primers are shown in Table 2 below. In addition, the expression levels of mTNFα, mIL-6, mIL-1β, MCP-1, and CXCL-5, which are inflammatory cytokine genes extracted from adipose tissues, were measured, and primers are shown in Table 3 below.

Figure 17:
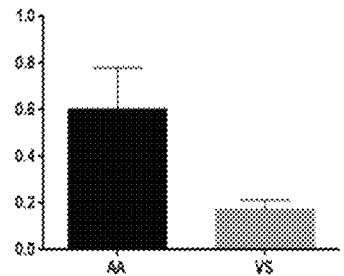
FIG. 17 shows the results, wherein to investigate the effect of VS_peptide (SEQ ID NO: 2) on the expression levels of metabolic genes, real-time PCR was performed using RNA extracted from liver tissues.
Figure 17:
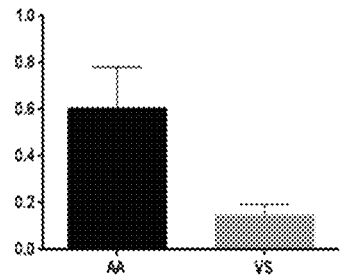
Figure 17:
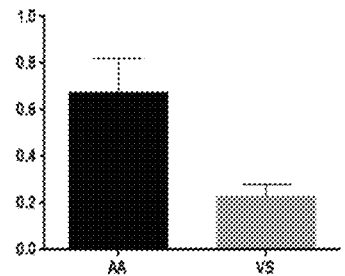
Figure 17:
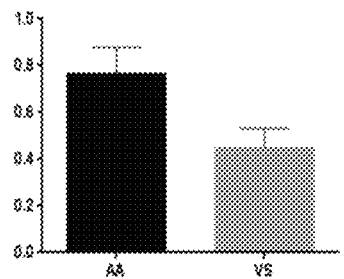
Figure 17:
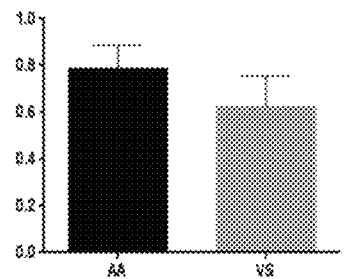
Figure 17:
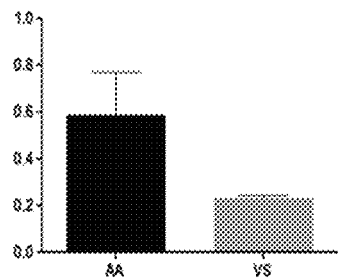
Figure 18:
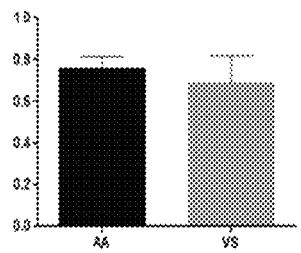
FIG. 18 shows the results, wherein to investigate the effect of VS_peptide (SEQ ID NO: 2) on the expression levels of inflammatory cytokine genes, real-time PCR was performed using RNA extracted from liver tissues.
Figure 18:
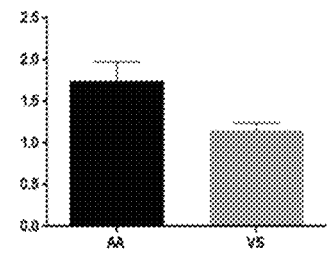
Figure 18:
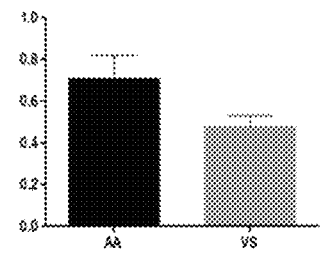
Figure 18:
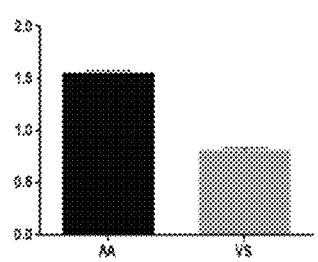
Figure 18:
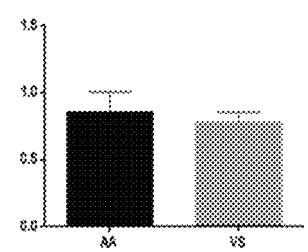

As a result, as shown in FIGS. 17 and 18, the expression levels of the metabolic genes and inflammatory cytokine genes were smaller in the treatment with VS_peptide_albumin (SEQ ID NO: 2) rather than the treatment with AA_peptide_albumin (SEQ ID NO: 3).

TABLE 2

Metabolic gene primers

| | | SEQ ID NO | |
|---|---|---|---|
| mPEPCK (Phosphoenol pyruvate Carboxykinase) | For | 10 | GGTATCCGGAC CACTTCTTGG |
| mPEPCK (Phosphoenol pyruvate Carboxykinase) | Rev | 11 | GGGGAGCAAGA TTAGAGCCC |
| mG6Pase (Glucose-6-phosphatase) | For | 12 | AAGAGCGCAAC AGTTCCCTT |
| mG6Pase (Glucose-6-phosphatase) | Rev | 13 | CTCTGGCCTCA CAATGGGTT |
| mPGC1a (PPAR-γ-co-activator-1a) | For | 14 | GTGTGTGCTGT GTGTCAGAGT |
| mPGC1a (PPAR-γ-co-activator-1a) | Rev | 15 | ACCACTTCAAT CCACCCAGA |
| mACC | For | 16 | AAAATGAAGGG GAACGACTGC |
| mACC | Rev | 17 | CAGTTCTGCCT GGAGGACCC |
| mFASN | For | 18 | AGGTGGCAGAG GTGCTGGCT |
| mFASN | Rev | 19 | GCGCAGGGTCG GAAGGGTTC |
| mSREBP1 | For | 20 | CCCAAGACTGC ACAATGCTG |

TABLE 2-continued

Metabolic gene primers

| | | SEQ ID NO | |
|---|---|---|---|
| mSREBP1 | REV | 21 | CTCTCAGGAGA GTTGGCACC |

TABLE 3

Inflammatory gene primers

| | | SEQ ID NO | |
|---|---|---|---|
| mTNFα (Tumor necrosis factor-α) | For | 22 | GTGACAAGCCT GTAGCCCAC |
| mTNFα (Tumor necrosis factor-α) | Rev | 23 | GCAGCCTTGTC CCTTGAAGA |
| mIL-6 (Interleukin-6) | For | 24 | CGGCCTTCCCT ACTTCACAA |
| mIL-6 (Interleukin-6) | Rev | 25 | TCTGCAAGTGC ATCATCGTT |
| mIL-β (Interleukin-β) | For | 26 | CAGGCTTGTGC TCTGCTTGT\ |
| mIL-β (Interleukin-β) | Rev | 27 | TGGGCCTCAAA GGAAAGAAT |
| MCP-1 | For | 28 | CAGGTCCCTGT CATGCTTCT |
| MCP-1 | Rev | 29 | CCCATTCCTTC TTGGGGTCA |
| CXCL5 | For | 30 | CCCCTTCCTCA GTCATAGCC |
| CXCL5 | Rev | 31 | TGGATCCAGAC AGACCTCCTT |

INDUSTRIAL APPLICABILITY

As set forth above, the present invention provides a polypeptide derived from CAP1 and a pharmaceutical composition containing the polypeptide as an active ingredient. The method of the present invention inhibits the binding of resistin and CAP1 and inhibits NF-κB activity, and thus can be favorably used in the prevention or treatment of an inflammatory disease, cancer, diabetes, atherosclerosis, a vascular disease, a cardiovascular disease, or heart failure.

The invention claimed is:

1. A peptide consisting of SEQ ID NO: 1 (GPPPPPVSTS), SEQ ID NO: 2 (PPPPGPPPPPVSTSSGSDES), SEQ ID NO: 4 (AAAAGPPPPPVSTSSGSDES), or SEQ ID NO: 5 (PPPPGAAAAAVSTSSGSDES), wherein the peptide inhibits the binding of adenylyl cyclase associated protein 1 (CAP1) and resistin.

2. The peptide of claim 1, wherein the inhibition of the binding is a competitive inhibition.

3. The peptide of claim 1, wherein the peptide inhibits the activity of an inflammatory cytokine.

4. The peptide of claim 1, wherein the peptide inhibits the activity of nuclear factor kappa B (NF-κB).

5. The peptide of claim 1, wherein the peptide induces the activity of AMP activated protein kinase (AMPK).

6. The peptide of claim 1, wherein the peptide inhibits the activity of protein kinase A (PKA).

7. A composition comprising the peptide of claim 1 as an active ingredient.

* * * * *